US011078157B1

(12) United States Patent
Pluth et al.

(10) Patent No.: US 11,078,157 B1
(45) Date of Patent: Aug. 3, 2021

(54) COMPOUND EMBODIMENTS THAT RELEASE H2S BY REACTION WITH A REACTIVE COMPOUND AND METHODS OF MAKING AND USING THE SAME

(71) Applicant: University of Oregon, Eugene, OR (US)

(72) Inventors: Michael D. Pluth, Eugene, OR (US); Matthew M. Cerda, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 16/262,281

(22) Filed: Jan. 30, 2019

Related U.S. Application Data

(60) Provisional application No. 62/624,609, filed on Jan. 31, 2018.

(51) Int. Cl.
| | | |
|---|---|---|
| *C07D 311/16* | (2006.01) | |
| *C07C 325/00* | (2006.01) | |
| *C07C 327/22* | (2006.01) | |
| *C07C 327/26* | (2006.01) | |
| *G01N 33/84* | (2006.01) | |

(52) U.S. Cl.
CPC .......... *C07C 325/00* (2013.01); *C07C 327/22* (2013.01); *C07C 327/26* (2013.01); *G01N 33/84* (2013.01)

(58) Field of Classification Search
CPC .................................................... C07D 311/16
See application file for complete search history.

(56) References Cited

U.S. PATENT DOCUMENTS

| | | | | |
|---|---|---|---|---|
| 4,399,075 | A * | 8/1983 | Yoshida | C07C 41/22 558/414 |
| 2002/0143202 | A1 | 10/2002 | Zhuang et al. | |
| 2007/0202198 | A1 | 8/2007 | Purcell | |
| 2008/0004245 | A1 | 1/2008 | Wallace et al. | |
| 2009/0184005 | A1 | 7/2009 | Zhang et al. | |
| 2010/0099683 | A1 | 4/2010 | Tomkinson et al. | |

FOREIGN PATENT DOCUMENTS

| | | |
|---|---|---|
| JP | 2737717 B2 | 4/1998 |
| WO | WO 2006/111791 | 10/2006 |
| WO | WO 2012/075242 | 6/2012 |
| WO | WO 2012/154126 | 11/2012 |
| WO | WO 2013/045951 | 4/2013 |
| WO | WO 2014/124205 | 8/2014 |

OTHER PUBLICATIONS

Voss et al. J. Chem. Research (S), 1997 252-253.*
Registry No. 88240-42-0. File Registry on STN, Nov. 16, 1984.*
Alajarin et al., "Benzylic Newman-Kwart rearrangement of O-azidobenzyl thiocarbamates triggered by phosphines: pseudopericyclic [1,3] shifts via uncoupled concerted mechanisms," *Tetrahedron*, 65(12): 2579-2590, Jan. 20, 2009.
Alajarin et al., "Intramolecular addition of benzylic radicals onto ketenimines. Synthesis of 2-alkylindoles," *Organic and Biomolecular Chemistry*, 1(23): 4282-4292, Oct. 23, 2003.
Bailey et al., "Chemiluminescent Detection of Enzymatically Produced Hydrogen Sulfide: Substrate Hydrogen Bonding Influences Selectivity for $H_2S$ over Biological Thiols," *J. Am. Chem. Soc.*, 135(44): 16697-16704, Oct. 4, 2013.
Benavides et al., "Hydrogen sulfide mediates the vasoactivity of garlic," *Proceedings of the National Academy of Sciences of the United States of America*, 104(46): 17977-17982, Nov. 13, 2007.
Braverman et al., "The Rearrangement of Furfuryl Dimethylthionocarbamates," *International Journal of Sulfur Chemistry*, 8(55): 1973.
Cerda et al "Dithioesters: simple, tunable, cysteine-selective $H_2S$ donors," Chem. Sci., Nov. 30, 2018.
Cerda et al "Thionoesters: A Native Chemical Ligation-Inspired Approach to Cysteine-Triggered H2S Donors," *J. Am. Chem. Soc.*, 2018, 140, 12574-12579, Sep. 19, 2018.
Cesarini et al., "Thiocarbamates as non-nucleoside HIV-1 reverse transcriptase inhibitors. Part 2: Parallel synthesis, molecular modelling and structure-activity relationship studies on analogues of O-(2-phenylethyl)-N-phenylthiocarbamate," *Biorg. Med. Chem.*, vol. 16, pp. 4173-4185, Dec. 25, 2007.
Chauhan et al., "Esterase Activated Carbonyl Sulfide/Hydrogen Sulfide ($H_2S$) Donors," *Org. Lett.*, 19(1): 62-65, Dec. 20, 2016.
Chitnis et al., "Pharmacological actions of the slow release hydrogen sulfide donor GYY4137 on phenylephrine-induced tong in isolated bovine ciliary artery," *Experimental Eye Research*, vol. 116, pp. 350-354, Nov. 2013.
Devarie-Baez et al., "Light-Induced Hydrogen Sulfide Release from 'Caged' gem-Dithiols," *Organic Letters*, 15(11): 2786-2789, May 22, 2013.
Gu et al., "Development of a boron-dipyrromethene-$Cu^{2+}$ ensemble based colorimetric probe toward hydrogen sulfide in aqueous media," *Tetrahedron Letters*, 52: 5000-5003, Sep. 2011.
Jarosz et al., "Microplate-Based Colorimetric Detection of Free Hydrogen Sulfide," *Analytical Chemistry*, 85(7): 3638-3643, Mar. 11, 2013.
Jensen et al., "Studies of Thioacids and Their Derivatives. IX. Thiosemicarbizides," *Acta Chemica Scandinavica*, vol. 22, pp. 1-50, 1968.
Jensen et al., "Studies of Thioacids and Their Derivatives. XV. (Alkoxythiocarbonyl)hydrazines and [(Alkylthio)thiocarbonyl]hydrazines," *Acta Chemica Scandinavica*, vol. 23, pp. 1916-1934, 1969.

(Continued)

*Primary Examiner* — Rebecca L Anderson
(74) *Attorney, Agent, or Firm* — Klarquist Sparkman, LLP

(57) ABSTRACT

Disclosed herein are embodiments of a donor compound that releases $H_2S$ by reacting with a reactive compound. The donor compound embodiments described herein can be used to deliver $H_2S$ to a subject or a sample and further can be used to administer therapeutic agents. The donor compound embodiments also can facilitate bioconjugation. Methods of making and using the donor compound embodiments also are disclosed.

2 Claims, 13 Drawing Sheets

(56) References Cited

OTHER PUBLICATIONS

Kashfi et al., "Biology and therapeutic potential of hydrogen sulfide and hydrogen sulfide-releasing chimeras," *Biochemical Pharmacology*, 85(5): 689-703, Mar. 1, 2013.

Kawanaka et al., "Design and Synthesis of Orally Bioavailable Inhibitors of Inducible Nitric Oxide Synthase. Part 1: Synthesis and Biological Evaluation of Dihydropyridin-2-imines," *Bioorganic & Medicinal Chemistry Letters*, vol. 12, pp. 2291-2294, 2002.

Kim et al., "Synthesis of Novel N-(2-Hydrophenyl)arylsulfonamides as Selective HDAC Inhibitory and Cytotoxic Agents," *Bulletin of the Korean Chemical Society*, 34(5):1487-1493, 2013.

Lee et al., "Analysis of structure-activity relationships for the 'B-region' of N-(4-t-butylbenzyl)-N'-[4-(methylsulfonylamino)benzyl]-thiourea analogues as TRPV1 antagonists," *Bioorganic and Medicinal Chemistry Letters*, 15(18): 4143-4150, Sep. 15, 2005.

Lee et al., "Detection of hydrogen peroxide with chemiluminescent micelles," *International Journal of Nanomedicine*, 3(4):471-476, Dec. 2008.

Li et al., "Characterization of a novel, water-soluble hydrogen sulfide-releasing molecule (GYY4137): New insights into the biology of hydrogen sulfide," *Circulation*, 117(18): 2351-2360, May 6, 2008.

Lippert et al., "Reaction-Based Fluorescent Probes for Selective Imaging of Hydrogen Sulfide in Living Cells," *Journal of the American Chemical Society*, 133(26): 10078-10080, Jun. 15, 2011.

Liu et al., "A visible light excitable colorimetric and fluorescent ESIPT probe for rapid and selective detection of hydrogen sulfide," *Organic & Biomolecular Chemistry*, 12:438-445, Nov. 6, 2013.

Liu et al., "Capture and Visualization of Hydrogen Sulfide by a Fluorescent Probe," *Angew. Chem. Int. Ed.*, 123(44):10327-10329, Sep. 6, 2011.

Maity et al., "A probe for ratiometric near-infrared fluorescence and colorimetric hydrogen sulfide detection and imaging in living cells," *RSC Advances* vol. 4, pp. 11147-11151, Feb. 10, 2014.

Martelli et al., "Arylthioamides as H2S Donors: L-Cysteine-Activated Releasing Properties and Vascular Effects in Vitro and in Vivo," *ACS Medicinal Chemistry Letters*, 4(10): 904-908, Aug. 8, 2013.

Montoya et al., "Selective turn-on fluorescent probes for imaging hydrogen sulfide in living cells," *Chemical Communications*, vol. 48, pp. 4767-4769, Mar. 16, 2012.

Montoya et al., "Development of Selective Colorimetric Probes for Hydrogen Sulfide Based on Nucleophilic Aromatic Substitution," *J. Org. Chem.*, 78(13): 6550-6557, Jun. 4, 2013.

Nishiyama et al., "Addition Reaction of Deoxygenation of Alcohols Using Isothiocyanates and Triethylsilane-DTBP," *Tetrahedron Letters*, 34(23): 3745-374, Feb. 22, 1993.

Olson et al., "A Practical Look at the Chemistry and Biology of Hydrogen Sulfide," *Antioxidants & Redox Signaling*, 17(1): 32-44, Jan. 16, 2012.

Peng et al., "A Fluorescent Probe for Fast and Quantitative Detection of Hydrogen Sulfide in Blood," *Angew. Chem. Int. Ed.*, 50(41): 9672-9675, Oct. 4, 2011.

Qian et al., "Selective fluorescent probes for live-cell monitoring of sulphide," *Nature Communications*, 2(495): 1-7, Oct. 11, 2011.

Roda et al., "Analytical chemiluminescence and bioluminescence: latest achievements and new horizons," *Analytical and Bioanalytical Chemistry*, 402(1) :69-76, Oct. 16, 2011.

Saha et al., "A colorimetric and fluorometric BODIPY probe for rapid, selective selection of $H_2S$ and its application in live cell imaging," *Organic & Biomolecular Chemistry*, vol. 11, pp. 8166-8170, Oct. 22, 2013.

Sasakura et al., "Development of a Highly Selective Fluorescence Probe for Hydrogen Sulfide," *Journal of the American Chemical Society*, 133(45): 18003-18005, Oct. 14, 2011.

Seletsky et al., "Structurally simplified macrolactone analogues of halichondrin B," *Bioorganic and Medicinal Chemistry Letters*, 14(22): 5547-5550, Sep. 21, 2004.

Shen et al., "Measurement of plasma hydrogen sulfide in vivo and in vitro," *Free Radical Biology & Medicine*, 50(9): 1021-1031, Jan. 27, 2011.

Tomasova et al., "Effects of AP39, a novel triphenylphosphonium derivatised anethole dithioethione hydrogen sulfide donor, on rat haemodynamic parameters and chloride and calcium Ca(v)3 and RyR2 channels," *Nitric Oxide—Biology and Chemistry*, vol. 46, pp. 131-144, Dec. 30, 2014.

Van De Bittner et al., "In vivo imaging of hydrogen peroxide production in a murine tumor model with a chemoselective bioluminescent reporter," *PNAS*, 107(50):21316-21321, Dec. 14, 2010.

Wei et al., "NBD-based colorimetric and fluorescent turn-on probes for hydrogen sulfide," *Organic & Biomolecular Chemistry*, vol. 12, pp. 479-485, Oct. 29, 2013.

Whiteman et al., "Emerging role of hydrogen sulfide in health and disease: critical appraisal of biomarkers and pharmacological tools," *Clinical Science*, 121(11): 459-488, Aug. 9, 2011.

Wu et al., "A selective colorimetric and ratiometric fluorescent probe for hydrogen sulfide," *Organic & Biomolecular Chemistry*, vol. 10, pp. 8342-8347, Aug. 8, 2012.

Yamaguchi et al., "Evaluation of chemiluminescence reagents for selective detection of reactive oxygen species," *Analytica Chimica Acta*, 665(1): 74-78, Mar. 19, 2010.

Yu et al., "Study on Cyclometalated Palladium-azo Complexes as Colorimetric Probes for Hazardous Gas in Water," *Chinese J. Chem.*, 25(6): 797-801, Jun. 14, 2007.

Zhang et al., "A dicopper complex chemiluminescence probe for the determination of thiols in the extracts of murine P388 lymphocytic leukemia cell," *Chem. Comm.*, No. 37, pp. 5624-5626, Aug. 18, 2009.

Zhang et al., "Highly selective and sensitive colorimetric probe for hydrogen sulfide by a copper (II) complex of azo-dye based on chemosensing ensemble approach," *Spectrochimica Acta Part A: Molecular and Biomolecular Spectroscopy*, vol. 90, pp. 35-39, Jan. 16, 2012.

Zhang et al., "On-Site Visual Detection of Hydrogen Sulfide in Air Based on Enhancing the Stability of Gold Nanoparticles," *ACS Applied Materials & Interfaces*, 6(9):6300-6307, Apr. 22, 2014.

Zhao et al. "Colorimetric Carbonyl Sulfide (COS)/Hydrogen Sulfide ($H_2S$) Donation from g-Ketothiocarbamate Donor Motifs," Angew. Chem. Int. Ed. Oct. 1, 2018.

Zhao et al., "A highly selective colorimetric chemodosimeter for fast and quantitative detection of hydrogen sulfide," *Analyst*, 137(23):5576-5580, Sep. 25, 2012.

Zhao et al., "Cysteine-Activated Hydrogen Sulfide (H2S) Donors," *Journal of the American Chemical Society*, 133(1): 15-17, Jan. 12, 2011.

Zhou et al., "Thioglycine and L-thiovaline: Biologically active H2S-donors," *Bioorganic & Medicinal Chemistry*, 20(8): 2675-2678, Feb. 27, 2012.

Chen et al., "Synthesis and anti-HBV activity of S-substituted 7-mercapto-4-methylcoumarin analogs," *Chinese Chemical Letters*, vol. 19, pp. 925-927, Aug. 2008.

\* cited by examiner

COMPOUND EMBODIMENTS THAT RELEASE H2S BY REACTION WITH A REACTIVE COMPOUND AND METHODS OF MAKING AND USING THE SAME

CROSS REFERENCE TO RELATED APPLICATION

This application claims the benefit of the earlier filing date of U.S. Provisional Application No. 62/624,609, filed on Jan. 31, 2018; this prior application is incorporated herein in its entirety.

ACKNOWLEDGMENT OF GOVERNMENT SUPPORT

This invention was made with government support under Contract No. R01GM113030 awarded by the National Institutes of Health. The government has certain rights in the invention.

FIELD

The present disclosure concerns embodiments of a donor compound that releases $H_2S$ upon ligation of a reactive compound, as well as embodiments of methods for making and using the donor compound embodiments.

BACKGROUND

Hydrogen sulfide has been recognized as an important biological molecule and plays important biological and pharmacological roles in different conditions associated with human health. For example, $H_2S$ has been implicated in hypertension, diabetes, diseases of mental deficiency, asthma, stroke, and other conditions. For example, administration of $H_2S$ results in reduction in blood pressure in hypertensive mice.

Although convenient, direct administration of $H_2S$ or sulfide-containing salts leads to a large burst of released $H_2S$, which is quickly metabolized/oxidized by cellular components as part of a toxicological response, and merely results in a disruption of redox homeostasis rather than elevated $H_2S$ levels. There exists a need in the art for an $H_2S$ delivery platform that provides the ability to control the amount and speed of $H_2S$ delivery.

SUMMARY

Disclosed herein are embodiments of a donor compound. The donor compound embodiments are capable of releasing $H_2S$ after reacting with a reactive compound. The donor compounds also can be used to simultaneously (or substantially simultaneously) label biomolecules while releasing $H_2S$. The structures of the donor compound embodiments are described herein. Also disclosed herein are embodiments of a pharmaceutical composition comprising the donor compound embodiments. Further disclosed are embodiments of a method for using the donor compounds, such as method embodiments for treating a subject that has or is at risk of developing a disease associated with $H_2S$ deficiency or $H_2S$ misregulation and/or a disease associated with carbonic anhydrase overexpression. Also disclosed herein are embodiments of a method for labeling a biomolecule using the donor compound embodiments.

The foregoing and other objects and features of the present disclosure will become more apparent from the following detailed description, which proceeds with reference to the accompanying figures.

BRIEF DESCRIPTION OF THE DRAWINGS

FIGS. 8A-8C show results from analyzing $H_2S$ release by compound 604a in the presence of increasing cysteine concentrations (250, 500, 1000, and 1250 μM) (FIG. 8A), and also showing plots of $\log(k_{obs})$ vs $\log([Cys])$ (FIG. 8B) and [Cys] vs. $k_{obs}$ (FIG. 8C) for compound 604a.

FIGS. 11A-11C show results from analyzing the release of $H_2S$ from compound 506a (25 μM) in the presence of increasing cysteine concentrations (250, 500, 1000, and 1250 μM) (FIG. 11A), and also showing plots of $\log(k_{obs})$ vs $\log([Cys])$ (FIG. 11B) and [Cys] vs. $k_{obs}$ (FIG. 8C) for compound 506a.

FIG. 15 is a potential energy surface diagram for the attack of cysteine thiolate on compound 506a.

DETAILED DESCRIPTION

I. Overview of Terms

Figure 1:
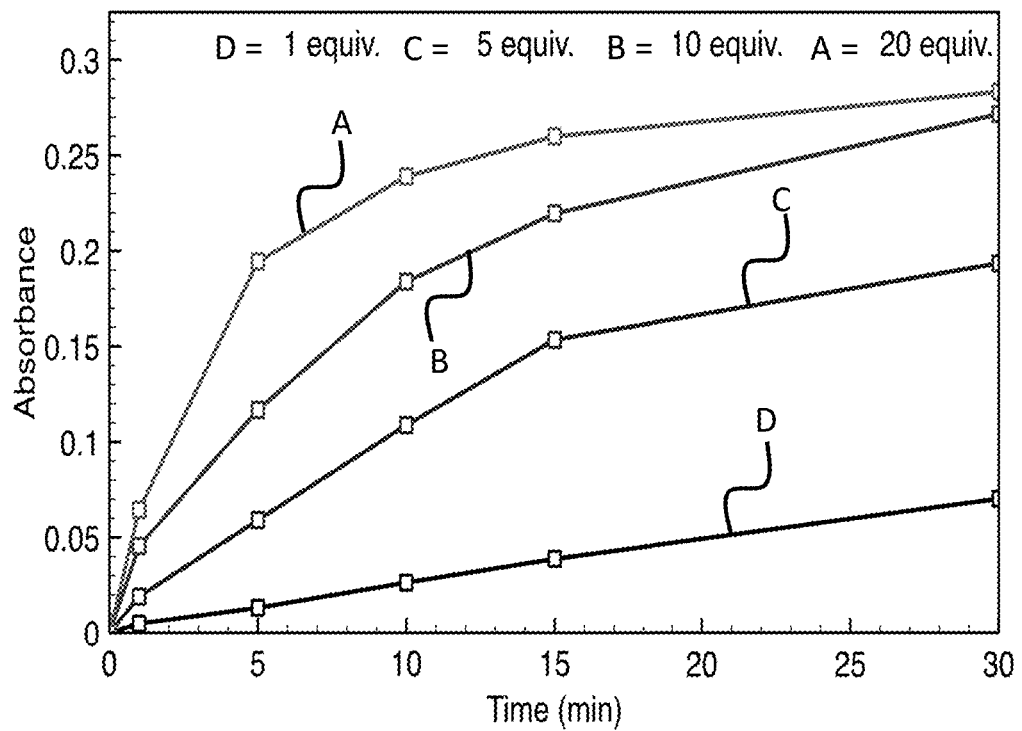
FIG. 1 is a plot showing the increased absorbance in a $H_2S$-responsive methylene blue assay when 25 μM of compound 604a is treated with increasing amounts of cysteine; the plot demonstrates the dose-dependent release of $H_2S$ from donor compound embodiments treated with cysteine.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the donor compound to which it is bound. Also, a dashed bond (i.e., "---") as used in certain formulas described herein indicates an optional bond (that is, a bond that may or may not be present). A person of ordinary skill in the art would recognize that the definitions provided below and the donor compounds and formulas included herein are not intended to include impermissible substitution patterns (e.g., methyl substituted with 5 different groups, and the like). Such impermissible substitution patterns are easily recognized by a person of ordinary skill in the art. In formulas and donor compounds disclosed herein, a hydrogen atom is present and completes any formal valency requirements (but may not necessarily be illustrated) wherever a functional group or other atom is not illustrated. For example, a phenyl ring that is drawn as

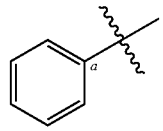 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aromatic: An aromatic group that is or can be coupled to a compound disclosed herein, wherein the aromatic group is or becomes coupled through an aliphatic group.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_{2-50}$, such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkyl-aryl/Alkenyl-aryl/Alkynyl-aryl: An aryl group that is or can be coupled to a compound disclosed herein, wherein the aryl group is or becomes coupled through an alkyl, alkenyl, or alkynyl group, respectively.

Alkyl-heteroaryl/Alkenyl-heteroaryl/Alkynyl-heteroaryl: A heteroaryl group that is or can be coupled to a compound disclosed herein, wherein the heteroaryl group is or becomes coupled through an alkyl, alkenyl, or alkynyl group, respectively.

Alkynyl: An unsaturated monovalent hydrocarbon having at least two carbon atom to 50 carbon atoms ($C_{2-50}$, such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —C(O)NR$^a$R$^b$ or —NR$^a$COR$^b$ wherein each of R$^a$ and R$^b$ independently is selected from hydrogen, aliphatic, heteroaliphatic, haloaliphatic, haloheteroaliphatic, aromatic, or any combination thereof.

Amine: —NR$^a$R$^b$, wherein each of R$^a$ and R$^b$ independently is selected from hydrogen, aliphatic, heteroaliphatic, haloaliphatic, haloheteroaliphatic, aromatic, or any combination thereof.

Amine-terminated Compound: A representative heteroatom-terminated compound eliminated or displaced from a donor compound embodiment after a reaction between a reactive compound and the donor compound. Amine-terminated compounds comprise a terminal amine group that is obtained from the fragmentation or bond breaking of the carbon-nitrogen bond present in a "—C(=S)V—" group of the donor compounds described herein, wherein V is NR$^1$.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example

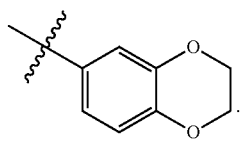 [SMILES: *c1ccc2c(c1)OCCO2]

However, in certain examples, context or express disclosure may indicate that the point of attachment is through a non-aromatic portion of the condensed ring system. For example,

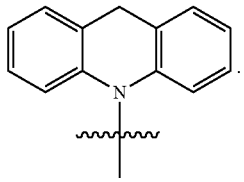 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g., S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, heteroaliphatic, aromatic, other functional groups, or any combination thereof.

Carboxyl: —C(O)OH or an anion thereof.

Detectable Label: A component of a donor compound embodiment that becomes conjugated to a reactive compound after reaction between the reactive compound and the donor compound embodiment and that is capable of producing a detectable signal and/or a specific binding reaction between a separate chemical component.

Detectable Moiety: A component of a donor compound embodiment that provides a detectable signal. In some embodiments, the detectable moiety can provide the detectable signal when attached to a donor compound embodiment. In some embodiments, the detectable moiety can provide the detectable signal when cleaved from a donor compound embodiment.

Detectable Signal: A signal (e.g., a color change, an increase or decrease in fluorescence, an increase or decrease in phosphorescence or other type of luminescence, and the like) that occurs (or is quenched) when a donor compound disclosed herein comprising a detectable moiety (e.g., a fluorophore or a dye) reacts with a reactive compound.

Disulfide: —SSR$^a$, wherein R$^a$ is selected from hydrogen, aliphatic, heteroaliphatic, haloaliphatic, haloheteroaliphatic, aromatic, or any combination thereof.

Electron-Donating Group: A functional group capable of donating at least a portion of its electron density into the ring to which it is directly attached, such as by resonance. Representative and non-limiting examples of electron-withdrawing groups can include alkoxy, thioether, amine (e.g., primary, secondary, or tertiary amine), hydroxyl, thiol, ether, acyloxy, aliphatic (e.g., alkyl, alkenyl, or alkynyl), aryl, aliphatic-aryl, heteroaliphatic-aryl.

Electron-Withdrawing Group: A functional group capable of accepting electron density from the ring to which it is directly attached, such as by inductive electron withdrawal. Representative and non-limiting examples of electron-withdrawing groups can include aldehyde, ketone, ester, carboxylic acid, acyl, a quaternary amine, acyl halide, cyano, sulfonate, nitro, nitroso, pyridinyl, alkyl halide, halogen (e.g., chloro, bromo, fluoro, or iodo), haloaliphatic, ammonium, or amide.

Ester: —C(O)OR$^a$ wherein R$^a$ is aliphatic, heteroaliphatic, haloaliphatic, haloheteroaliphatic, aromatic, or any combination thereof; or —OC(O)R$^a$, wherein R$^a$ is selected from hydrogen, aliphatic, heteroaliphatic, haloaliphatic, haloheteroaliphatic, aromatic, or any combination thereof.

Fluorophore: A functional group or portion of a donor compound (e.g., a heteroatom-terminated group) that causes the donor compound, a composition, or a labeled biomolecule to fluoresce when exposed to an excitation source. Exemplary fluorophores are described herein.

Haloaliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroaliphatic-aryl: An aryl group that is or can be coupled to a compound disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroalkyl-aryl/Heteroalkenyl-aryl/Heteroalkynyl-aryl: An aryl group that is or can be coupled to a compound disclosed herein, wherein the aryl group is or becomes coupled through a heteroalkyl, heteroalkenyl, or heteroalkynyl group, respectively.

Heteroalkyl-heteroaryl/Heteroalkenyl-heteroaryl/Heteroalkynyl-heteroaryl: A heteroaryl group that is or can be coupled to a compound disclosed herein, wherein the aryl group is or becomes coupled through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, aromatic, other functional groups, or any combination thereof.

Heteroatom: An atom other than carbon or hydrogen, such as (but not limited to) oxygen, nitrogen, sulfur, silicon, boron, selenium, or phosphorous. In particular disclosed embodiments, such as when valency constraints do not permit, a heteroatom does not include a halogen atom.

Heteroatom-Terminated Compound: A compound eliminated or displaced from a donor compound embodiment upon exposing the donor compound to a reactive compound. In some embodiments, the heteroatom-terminated compound can comprise the V group (or V—$R^1$ group) of the formulas described herein after breaking the bond between the V group (or V—$R^1$ group) and the carbon atom to which it is bound, wherein V is an oxygen atom, a nitrogen atom, a sulfur atom, or other heteroatom, the heteroatom-terminated compound further comprising the $R^2$ group bound to V in the formulas described herein. In some embodiments, the heteroatom-terminated compound can emit a detectable signal or can be (or can comprise) a therapeutic agent.

Hydroxy-terminated Compound: A representative heteroatom-terminated eliminated or displaced from a donor compound embodiment after a reaction between a reactive compound and the donor compound. Hydroxy-terminated compounds comprise a terminal hydroxyl group that is obtained from the fragmentation or bond breaking of the carbon-oxygen bond present in a "—C(=S)V—" group of the donor compounds described herein, wherein V is O.

Ketone: —C(O)$R^a$, wherein $R^a$ is selected from aliphatic, heteroaliphatic, aromatic, any combination thereof.

Lower Aliphatic: An aliphatic group having 1 to 10 carbon atoms, such as 1 to 8 carbon atoms, or 1 to 6 carbon atoms, or 1 to 4 carbon atoms. In some embodiments, lower aliphatic includes lower alkyl groups, such as methyl, ethyl, propyl, isopropyl, butyl, and isobutyl, tert-butyl.

Pharmaceutically Acceptable Excipient: A substance, other than a donor compound that is included in a formulation of the donor compound. As used herein, an excipient may be incorporated within particles of a pharmaceutical composition, or it may be physically mixed with particles of a pharmaceutical composition. An excipient also can be in the form of a solution, suspension, emulsion, or the like. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethylene glycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin. In independent embodiments, water is not intended as a pharmaceutically acceptable excipient.

Reactive Compound: A compound that reacts (typically via nucleophilic attack) with a donor compound embodiment so as to initiate $H_2S$ release from the donor compound embodiment. In particular disclosed embodiments, the reactive compound can comprise two functional groups capable of forming bonds with the donor compound embodiment. In some embodiments, the two functional groups capable of forming bonds with the donor compound embodiment can be provided by the same reactive compound or they can be provided by two different reactive compound embodiments.

Saccharide: A sugar that can be selected from monosaccharides, disaccharides, oligosaccharides, and/or polysaccharides.

Solubilizing Agent: An agent that increases the solubility of a donor compound disclosed herein in aqueous media. Solubilizing agents can be selected from, but are not limited to, sodium bicarbonate, glucose, polyalkylene ethers or glycols (e.g., polyethylene glycol, polypropylene glycol, and the like), surfactants (e.g., sorbitan esters), and other solubilizing agents known in the art.

Subject: Mammals and other animals, such as humans, companion animals (e.g., dogs, cats, rabbits, etc), utility animals, and feed animals; thus, disclosed methods are applicable to both human therapy and veterinary applications.

Sulfonate: —SO$_3^-$, wherein the negative charge of the sulfonate group may be balanced with an M$^+$ counter ion, wherein M$^+$ may be an alkali ion, such as K$^+$, Na$^+$, Li$^+$; an ammonium ion, such as $^+$N(R$^b$)$_4$ where R$^b$ is H, aliphatic, heteroaliphatic, haloaliphatic, haloheteroaliphatic, or aromatic; or an alkaline earth ion, such as [Ca$^{2+}$]$_{0.5}$, [Mg$^{2+}$]$_{0.5}$, or [Ba$^{2+}$]$_{0.5}$.

Sulfonyl: —SO$_2$R$^a$, wherein R$^a$ is selected from hydrogen, aliphatic, heteroaliphatic, haloaliphatic, haloheteroaliphatic, aromatic, or an organic functional group.

Targeting Group: A group that is capable of targeting a cell, an organelle, or the like and thereby directing the donor compound comprising the targeting group to the cell, organelle, or the like. In some embodiments, a targeting group can be morpholine or a derivative thereof, a phosphonium or phosphine group, a quaternary amine, or the like. Other targeting components can include thiol or hydroxyl functional groups, which can be used to target surfaces or monolayers.

Thio-terminated Compound: A representative heteroatom-terminated eliminated or displaced from a donor compound embodiment after a reaction between a reactive compound and the donor compound. Thio-terminated compounds comprise a terminal thiol group that is obtained from the fragmentation or bond breaking of the carbon-sulfur bond present in a "—C(═S)V—" group of the donor compounds described herein, wherein V is S.

Treating/Treatment: Treatment of a disease or condition of interest in a subject, particularly a human or canine having the disease or condition of interest, and includes by way of example, and without limitation:

(i) prophylactic administration to prevent the disease or condition from occurring in a subject, or to ameliorate symptoms associated with the condition if required in particular, when such subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

II. Introduction

Disclosed herein are embodiments of a donor compound that donates (that is, releases) H$_2$S upon reaction with a reactive compound. The donor compound embodiments described herein serve as new and efficient tools for increasing the amount of H$_2$S in biological contexts and thus can be used to treat subjects in need of increased H$_2$S production and/or to improve neurotransmission and cardiovascular health in subjects. In some embodiments, the donor compounds described herein can serve as research tools to further explore the role of H$_2$S in biology. The donor compounds described herein are responsive to reactive compounds, such as biological reactive compounds like cysteine, homocysteine, or the like, even at physiological pH. The donor compound's unique structure also provides a novel means for tuning the rate of H$_2$S release. The donor compound embodiments also can be used to facilitate bioconjugation of detectable labels to biomolecules and/or to deliver therapeutic agents.

III. Compound Embodiments

Disclosed herein are embodiments of a donor compound capable of releasing H$_2$S. In particular disclosed embodiments, the donor compound is capable of reacting with a reactive compound that facilitates H$_2$S release from the compound. In some embodiments, the donor compound can be configured to comprise a detectable moiety, a therapeutic agent, a sugar, or the like and can release such components in addition to releasing H$_2$S. In yet additional embodiments, the donor compound can be configured to comprise a detectable label and can be used to label biomolecules with the detectable label in addition to releasing H$_2$S. In yet additional embodiments, the donor compound can comprise targeting groups that facilitate delivery of the donor compound to a particular region in a sample and/or in a subject. As such, the donor compound is able to release H$_2$S in these particular regions.

In particular disclosed embodiments, the donor compound embodiments have a structure satisfying Formula I.

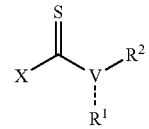

Formula I

With reference to Formula I, the following variable recitations can apply in any combination:

X can be hydrogen, aliphatic, heteroaliphatic, haloaliphatic, haloheteroaliphatic, aromatic, and any combination thereof;

V can be a heteroatom and in an independent embodiment is a heteroatom other than nitrogen;

R$^1$, if present (such as when V is a heteroatom other than oxygen or sulfur), can be selected from hydrogen, aliphatic, haloaliphatic, haloheteroaliphatic, heteroaliphatic, aromatic, or any combination thereof; and R$^2$ can be aliphatic, heteroaliphatic, haloaliphatic, haloheteroaliphatic, aromatic, or any combination thereof; or, together with R$^1$ and V, can provide a heterocyclic group, such as in embodiments where R$^1$ is present.

In some embodiments of Formula I, the following variable recitations can apply in any combination:

X can be aliphatic (e.g., alkyl, alkenyl, or alkynyl), aryl (e.g., phenyl or naphthyl), heteroaryl (e.g., pyridinyl, indolyl, pyrimidinyl, imidazolyl, or other heteroaryl compounds), a detectable label (such as a fluorophore, a quantum dot, or a member of a specific binding pair), or any combination thereof. In some embodiments, the detectable label may be directly or indirectly bound to the carbon atom of the C═S group illustrated in Formula I. In embodiments where X is indirectly coupled, a linker may be used to bind X to the carbon atom of the C═S group, wherein the linker can be aliphatic, heteroaliphatic, or aromatic;

V can be oxygen or sulfur; and

R² can be aliphatic (e.g., alkyl, alkenyl, alkynyl), heteroaliphatic (e.g., heteroalkyl, heteroalkenyl, heteroalkynyl), aromatic, aliphatic-aromatic, heteroaliphatic-aromatic, -aromatic-(R³)$_m$, aliphatic-aromatic-(R³)$_m$, or heteroaliphatic-aromatic-(R³)$_m$, wherein m can be an integer selected from 0-5 and each R³ independently is an electron-donating group, an electron-withdrawing group, a targeting group, a detectable moiety, or a therapeutic agent, such as an anti-inflammation drug (e.g., naproxen or other NSAID) or other small molecule therapeutics; or any combination thereof.

In yet additional embodiments of Formula I, the following variable recitations can apply in any combination;

X can be lower aliphatic, aryl, heteroaryl, biotin (directly or indirectly bound to the C═S group), a fluorophore (directly or indirectly bound to the C═S group), wherein the fluorophore can be selected from, but is not limited to, a xanthene derivative (e.g., fluorescein, rhodamine, eosin, Texas red, Oregon green, or the like), cyanine or a cyanine derivative (e.g., indocarbocyanine, oxacarbocyanine, thiacarbocyanine, or merocyanine), a naphthalene derivative (e.g., dansyl, prodan, and the like), coumarin and derivatives thereof (e.g., hydroxycoumarin, aminocoumarin, methoxycoumarin, and the like), oxadiazole derivatives (e.g., pyridyloxazole, nitrobenzoxadiazole, benzoxadiazole, and the like), anthracene derivatives, pyrene derivatives (e.g., cascade blue), oxazine derivatives (e.g., Nile red, Nile blue, cresyl violet, and the like), acridine derivatives (e.g., auramine, crystal violet, malachite green, and the like), and tetrapyrrole derivatives (e.g., porphin, phthalocyanine, and the like) and in some embodiments can be methylrhodol, 2-(2-methoxyethyl)-1H-benzo[de]isoquinoline-1,3(2H)-dione, 4-methyl-2H-chromen-2-one, coumarin, naphthalimide, fluorescein, rhodamine, rhodol, Cy3, or Cy5;

V is oxygen or sulfur; and

R² is aryl (e.g., phenyl or naphthyl); heteroaryl (e.g., pyridinyl, indolyl, pyrimidinyl, imidazolyl, or other heteroaryl compounds); aliphatic-aryl; aliphatic-heteroaryl; heteroaliphatic-aryl; heteroaliphatic-heteroaryl; or aliphatic-aryl-(R³)$_m$, aliphatic-heteroaryl-(R³)$_m$, heteroaliphatic-aryl-(R³)$_m$, heteroaliphatic-heteroaryl-(R³)$_m$, aryl-(R³)$_m$ or heteroaryl-(R³)$_m$ wherein m can be an integer selected from 0-5 and each R³ independently is aldehyde, ketone, ester (—COOR$^a$ or —OCOR$^a$), carboxylic acid, acyl, acyl halide, cyano, sulfonate, nitro, nitroso, pyridinyl, alkyl halide, halogen (e.g., chloro, bromo, fluoro, or iodo), haloaliphatic, ammonium, amide (—CONH$_2$ or —NHCOR$^a$), alkoxy, thioether, amine (e.g., primary, secondary, tertiary, or quaternary amine), hydroxyl, thiol, ether, acyloxy, aliphatic (e.g., alkyl, alkenyl, alkynyl), aryl, aliphatic-aryl, heteroaliphatic-aryl, a morpholine or a derivative thereof, a phosphonium or phosphine group, a quaternary amine, or the like, a fluorophore, an NSAID or other therapeutic agent, or any combinations thereof. In particular disclosed embodiments, R² can comprise a linker group, such as an aliphatic group or a heteroaliphatic group, which is used to bind a detectable moiety, a therapeutic agent, a targeting group, or the like to the donor compound.

In some embodiments, the donor compound can have a structure satisfying Formula IIA or IIB.

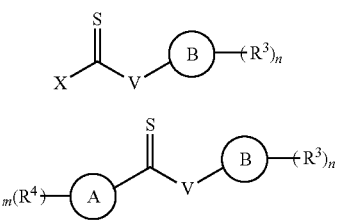

With reference to Formula IIA, X and V can be as recited above for any variable recitations provided for Formula I. With reference to Formula IIB, V can be as recited above for any variable recitations provided for Formula I. Furthermore, the following variable recitations can apply for Formulas IIA and/or IIB in any combination:

X can be aliphatic;

ring B can be aromatic, aliphatic-aromatic, or heteroaliphatic-aromatic;

ring A can be aromatic, aliphatic-aromatic, or heteroaliphatic-aromatic;

R³, if present (such as when n is not 0), is a substituent other than hydrogen;

R⁴, if present (such as when m is not 0), is a substituent other than hydrogen;

n can be an integer selected from 0 to 10, such as 0, 1, 2, 3, 4, 5, 6, 7, 8, 9, or 10; and m can be an integer selected from 0 to 10, such as 0, 1, 2, 3, 4, 5, 6, 7, 8, 9, or 10.

In yet additional embodiments, the following variable recitations can apply in any combination:

X can be lower aliphatic, aryl, heteroaryl, a detectable label (such as a fluorophore, a quantum dot, or a member of a specific binding pair), or any combination thereof. In some embodiments, the detectable label may be directly or indirectly bound to the carbon atom of the C═S group illustrated in Formula I. In embodiments where X is indirectly coupled, a linker may be used to bind X to the carbon atom of the C═S group, wherein the linker can be aliphatic, heteroaliphatic, or aromatic;

V can be oxygen or sulfur;

ring B can be aryl or heteroaryl;

ring A can be aryl or heteroaryl;

R³ can be aliphatic, heteroaliphatic, haloaliphatic, haloheteroaliphatic, aromatic, or any combination thereof and can be located at a position that is para, ortho, or meta relative to the bond to which R³ is bound to ring B;

R⁴ can be aliphatic, heteroaliphatic, haloaliphatic, haloheteroaliphatic, aromatic, or any combination thereof and can be located at a position that is para, ortho, or meta relative to the bond to which R³ is bound to ring A;

n can be an integer selected from 0 to 5, such as 0, 1, 2, 3, 4, or 5; and m can be an integer selected from 0 to 5, such as 0, 1, 2, 3, 4, or 5.

In yet additional embodiments, the following variable recitations can apply in any combination:

X can be lower alkyl;

ring B can be phenyl or naphthyl; or pyridinyl, indolyl, pyrimidinyl, imidazolyl, or other heteroaryl compounds;

ring A can be phenyl or naphthyl; or pyridinyl, indolyl, pyrimidinyl, imidazolyl, or other heteroaryl compounds;

R³ can be aldehyde, ketone, ester (—COOR$^a$ or —OCOR$^a$), carboxylic acid, acyl, acyl halide, cyano, sulfonate, nitro, nitroso, pyridinyl, alkyl halide, halogen (e.g., chloro, bromo, fluoro, or iodo), haloaliphatic, ammonium, amide (—CONH$_2$ or —NHCOR$^a$), alkoxy, thioether, amine (e.g., primary, secondary, tertiary, or quaternary amine), hydroxyl, thiol, ether, acyloxy, aliphatic (e.g., alkyl, alkenyl, alkynyl), aryl, -aliphatic-aryl, an NSAID or other therapeutic agent, or any combinations thereof; and R⁴ can be aldehyde; ketone; ester (—COOR$^a$ or —OCOR$^a$); carboxylic acid; acyl; acyl halide; cyano; sulfonate; nitro; nitroso; pyridinyl; alkyl halide; halogen (e.g., chloro, bromo, fluoro, or iodo); haloaliphatic; ammonium; amide (—CONH$_2$ or —NHCOR$^a$); alkoxy; thioether; amine (e.g., primary, secondary, tertiary, or quaternary amine); hydroxyl; thiol; ether; acyloxy; aliphatic (e.g., alkyl, alkenyl, alkynyl); aryl; -aliphatic-aryl; -linker-biotin (wherein the linker is an aliphatic or heteroaliphatic linker); biotin; -linker-fluorophore; or fluorophore, wherein the fluorophore is a xanthene derivative (e.g., fluorescein, rhodamine, eosin, Texas red, Oregon green, or the like), cyanine or a cyanine derivative (e.g., indocarbocyanine, oxacarbocyanine, thiacarbocyanine, or merocyanine), a naphthalene derivative (e.g., dansyl, prodan, and the like), coumarin and derivatives thereof (e.g., hydroxycoumarin, aminocoumarin, methoxycoumarin, and the like), oxadiazole derivatives (e.g., pyridyloxazole, nitrobenzoxadiazole, benzoxadiazole, and the like), anthracene derivatives, pyrene derivatives (e.g., cascade blue), oxazine derivatives (e.g., Nile red, Nile blue, cresyl violet, and the like), acridine derivatives (e.g., auramine, crystal violet, malachite green, and the like), and tetrapyrrole derivatives (e.g., porphin, phthalocyanine, and the like). In some embodiments, the fluorophore can be methylrhodol, 2-(2-methoxyethyl)-1H-benzo[de]isoquinoline-1,3(2H)-dione, 4-methyl-2H-chromen-2-one, coumarin, naphthalimide, fluorescein, rhodamine, rhodol, Cy3, or Cy5;

n can be 1, 2, 3, 4, or 5; and m can be 1, 2, 3, 4, or 5.

In some embodiments, the donor compound can have a structure satisfying any one or more of the following formulas:

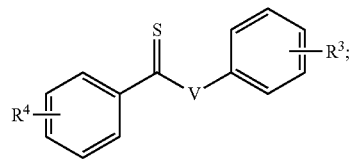
Formula IIIA

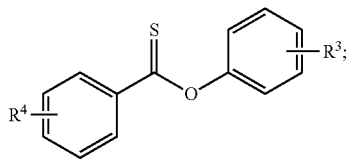
Formula IIIB

Formula IIIC

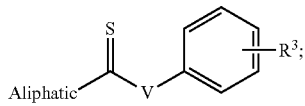
Formula IIID

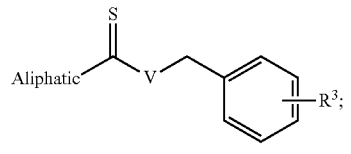
Formula IIIE

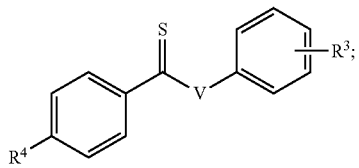
Formula IVA

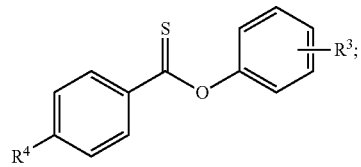
Formula IVB

Formula IVC

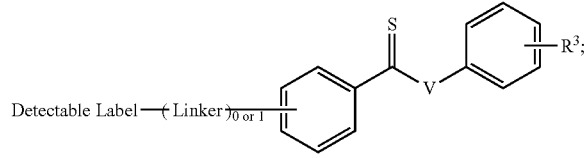
Formula VA

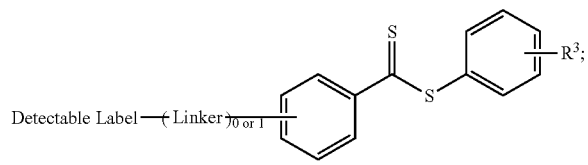
Formula VB
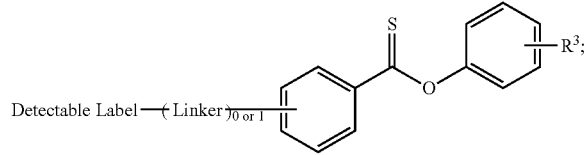
Formula VC
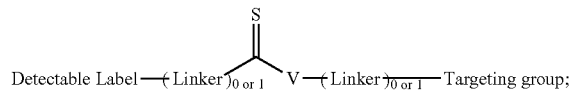
Formula VIA
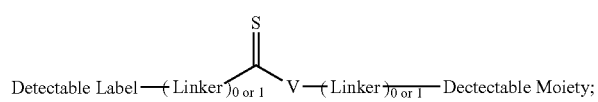
Formula VIB
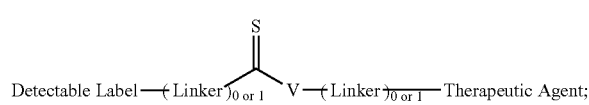
Formula VIC
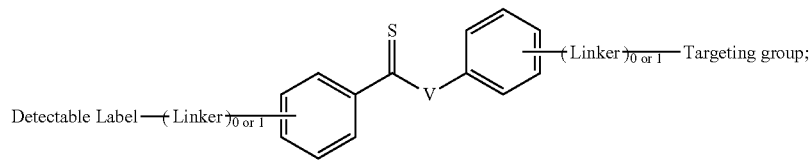
Formula VID
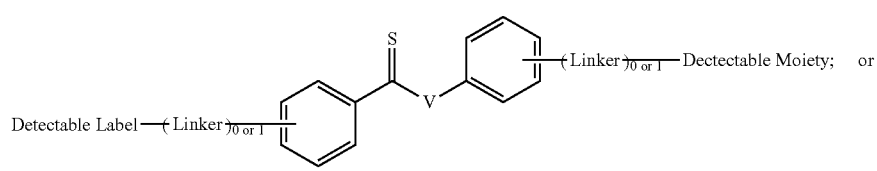
Formula VIE
or
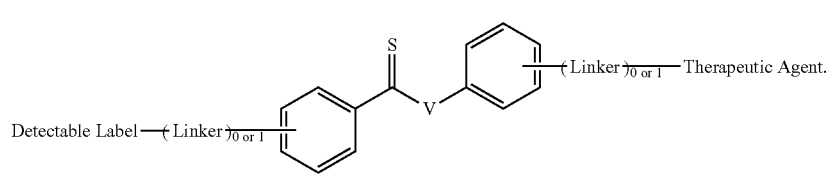
Formula VIF
In particular disclosed embodiments, the donor compound can be selected from the following:
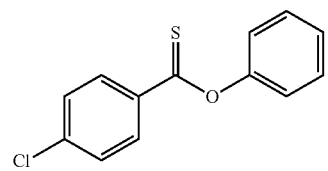
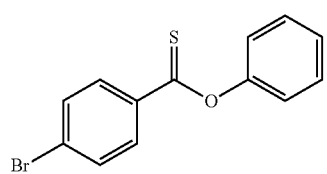
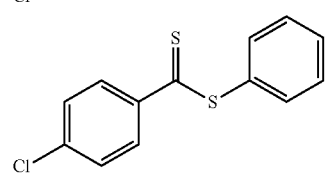
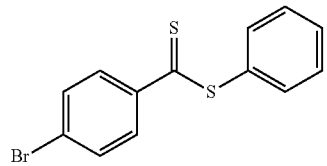

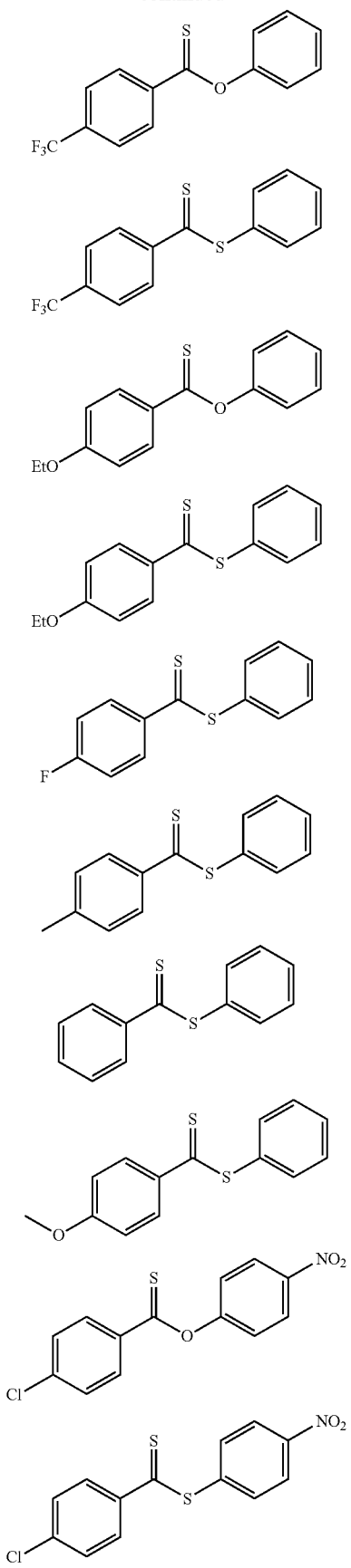
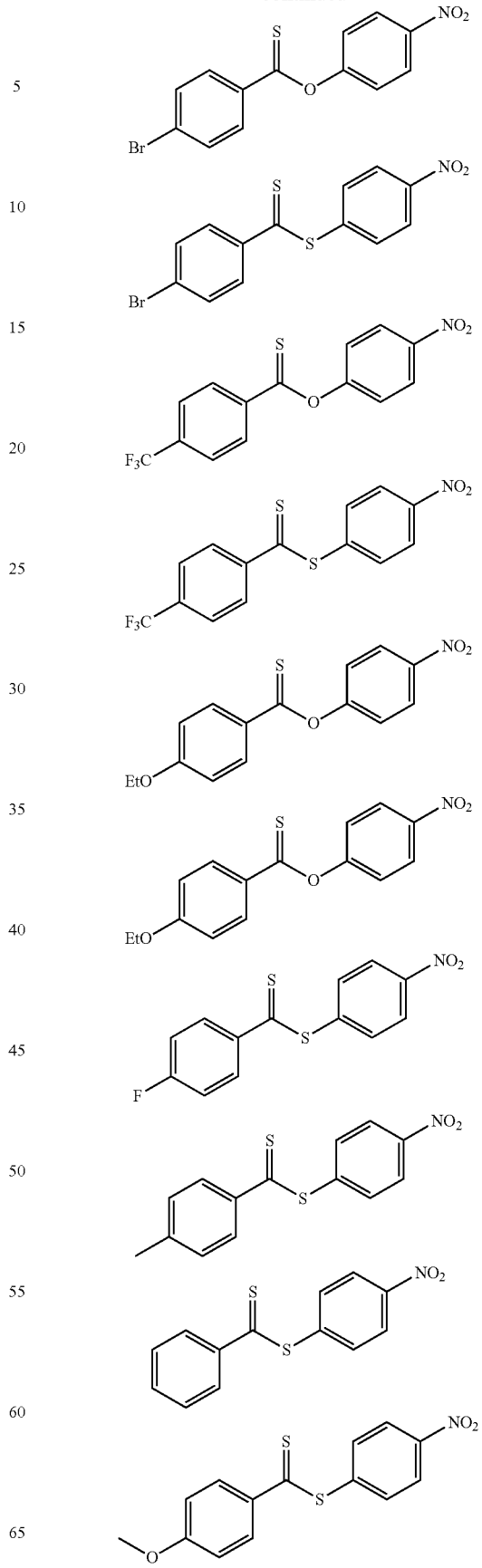

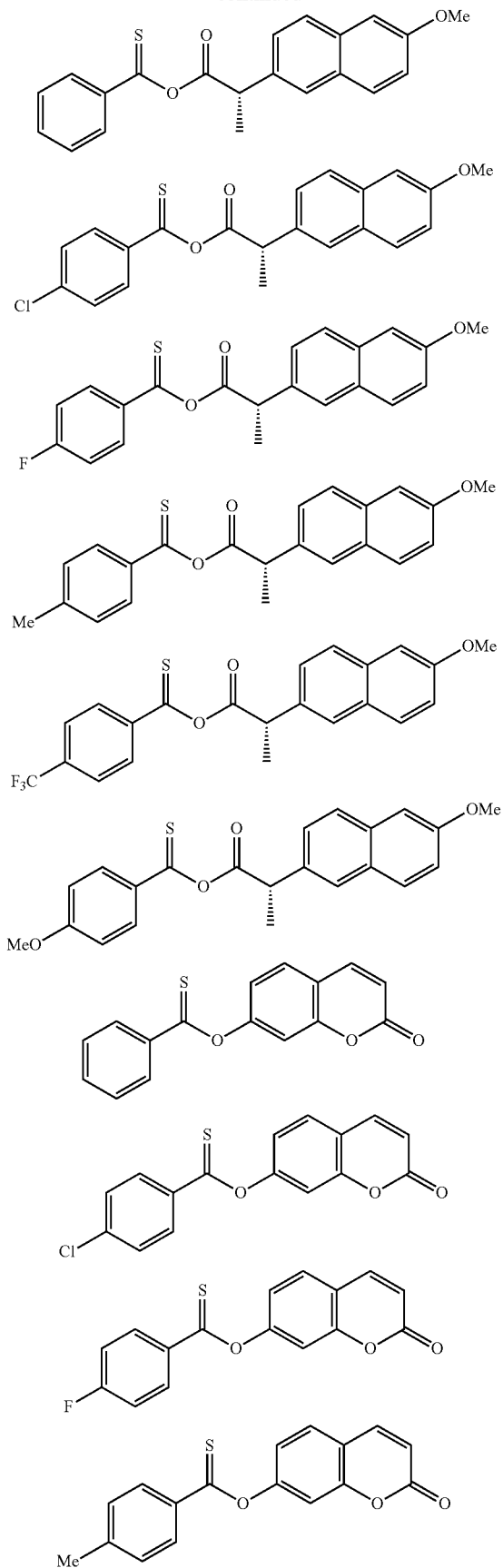
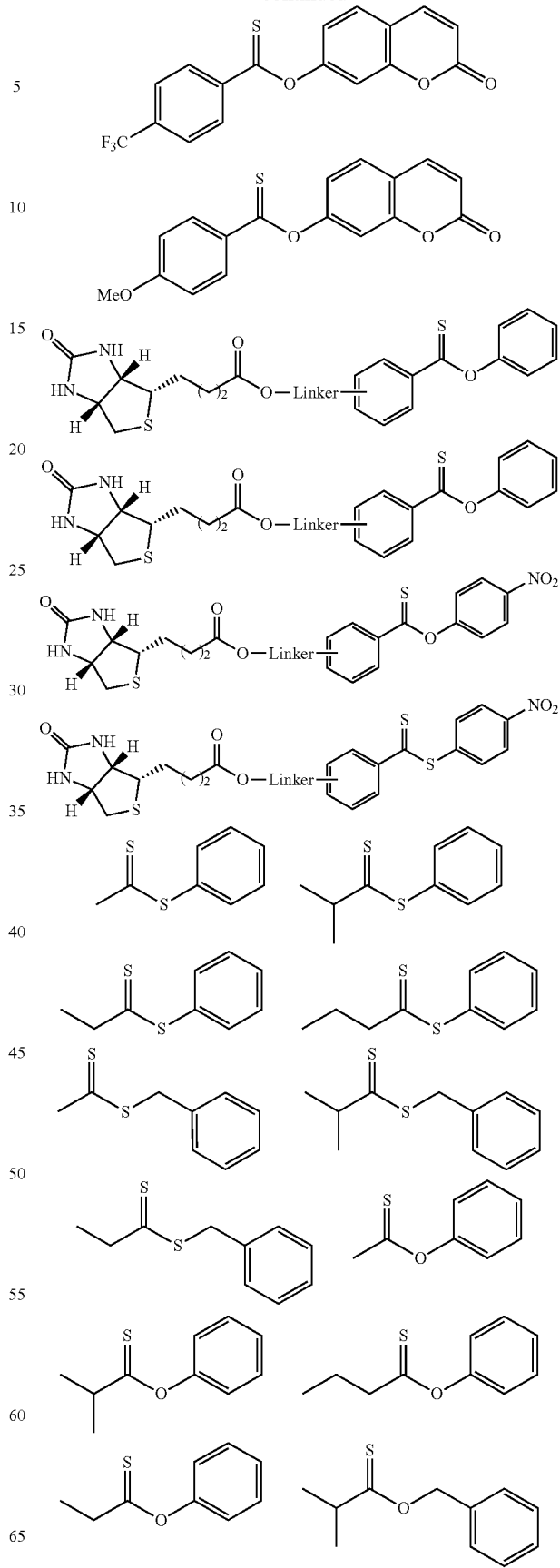

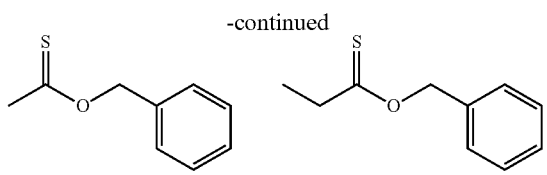

In an independent embodiment, the donor compound is not O-phenyl benzothioate, O-phenyl 4-methylbenzothioate, O-phenyl 4-methoxybenzothioate, or O-phenyl 4-fluorobenzothioate. Such donor compounds can, however be used in composition and/or method embodiments described herein. In yet another independent embodiment, the donor compound is not

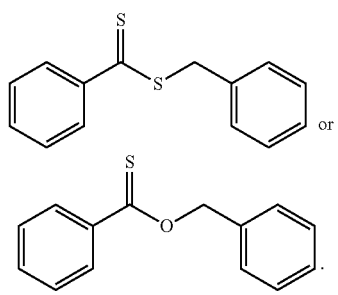

Composition embodiments comprising a donor compound also are disclosed herein. In some embodiments, the composition comprises a donor compound embodiment, or a plurality thereof. In some embodiments, the composition can further comprise water, a buffer, or any combination thereof. In some embodiments, the composition can be a pharmaceutical composition that comprises a donor compound and one or more pharmaceutically acceptable excipients, water, a pharmaceutically acceptable buffer, a separate therapeutic agent, or any combinations thereof. In some embodiments, the pharmaceutical composition comprises a donor compound comprising a therapeutic agent, such as certain donor compound embodiments described above.

Also disclosed herein are embodiments of a composition comprising one or more products formed from a donor compound after reaction with the reactive compound. Such composition embodiments also can comprise an amount of the donor compound, such as amounts of any unreacted donor compound embodiment. In particular disclosed embodiments, the composition can comprise a heteroatom-terminated compound (e.g., an amine-terminated compound, a hydroxy-terminated compound, or a thio-terminated compound); $H_2S$; a reactive compound conjugate, which is formed after reaction of the donor compound and the reactive component and after $H_2S$ has been released; or any combination thereof. The reactive compound conjugate is described in a subsequent section herein. In some embodiments, the composition comprises a heteroatom-terminated compound. In additional embodiments, the composition comprises $H_2S$. In yet additional embodiments, the composition comprises the reactive compound conjugate. In some embodiments, the composition comprises a heteroatom-terminated compound, $H_2S$, and the reactive compound conjugate. In some embodiments, the composition comprises a heteroatom-terminated compound and $H_2S$. In yet some additional embodiments, the composition comprises $H_2S$ and the reactive compound conjugate. In yet some additional embodiments, the composition comprises the heteroatom-terminated compound and the reactive compound conjugate.

Also disclosed herein are embodiments of a kit comprising a donor compound embodiment and further comprising a pharmaceutically acceptable excipient, a member of a specific binding pair, water, a reactive component, a buffer, or any combination thereof. In some embodiments, the donor compound can be in a container separated from the water, the reactive component, the buffer, and/or the conversion component. In some embodiments, the kit can include a separate container comprising the water, the reactive component, or the buffer; or the reactive component, water, and/or buffer can be provided by the user as a component separate from the kit. In some embodiments, the kit can further comprise a solubilizing agent, a filter, a multi-well plate, a test strip, a slide, a disc, or any combinations thereof.

IV. Method of Making Donor Compound Embodiments

Also disclosed herein are embodiments of a method for making the donor compound embodiments. In some embodiments, the donor compound embodiments can be made using the methods contemplated by Scheme 1.

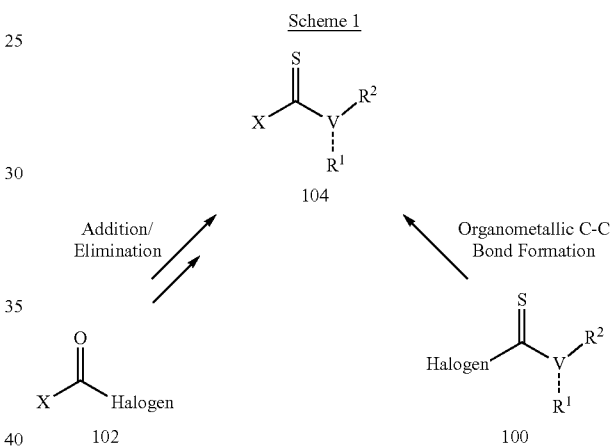

Scheme 1

In some embodiments, compound embodiments can be made using the method shown in Scheme 1A. With reference to Scheme 1A, donor compound embodiments 110 can be made by coupling a thiocarbonyl-containing starting material 106 with a Grignard component 108 comprising the X group illustrated in the formulas provided herein. In some embodiments, the thiocarbonyl-containing starting material can be obtained from a commercial source or can be made using methods known to those of ordinary skill in the art, particularly with the benefit of this disclosure. This coupling reaction can provide donor compound embodiments in one step.

Scheme 1A

In some embodiments, compound embodiments can be made using the method shown in Scheme 1B. With reference to Scheme 1B, acyl chloride starting compound 112 can be coupled with thiol 114 to provide thioester compound 116. Thioester compound 116 can be converted to dithioester compound 118 using Lawesson's reagent.

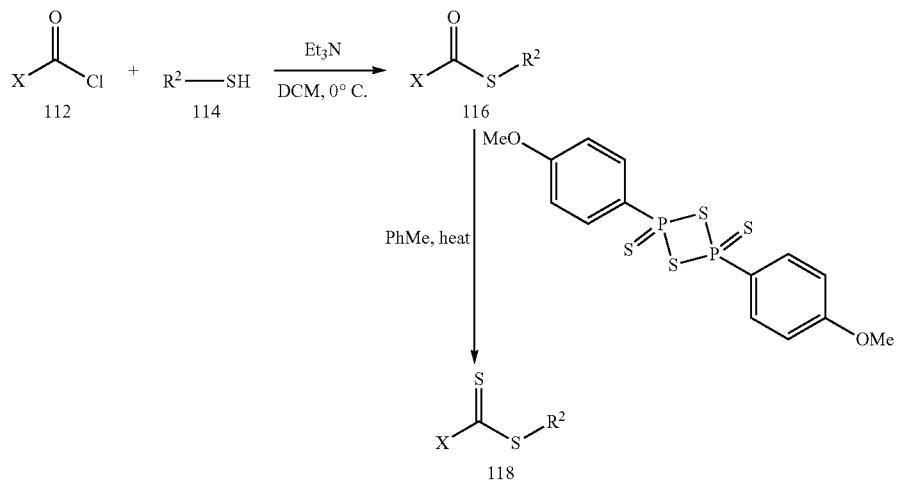
Additional embodiments of a method for making the donor compounds are illustrated below in Schemes 2-4.
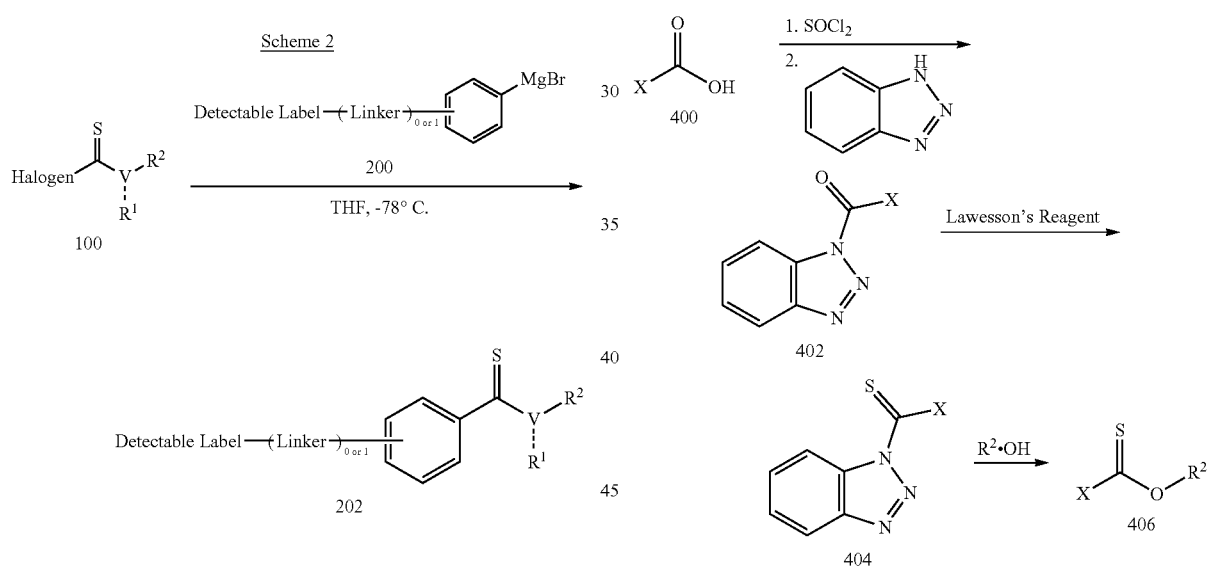
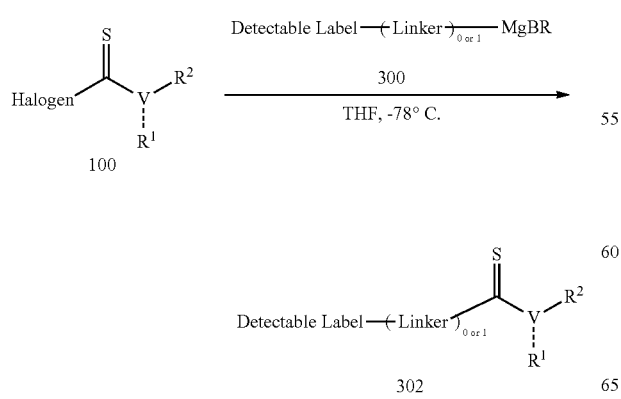
Representative compound embodiments can be made using the methods shown in Schemes 5 and 6 below.
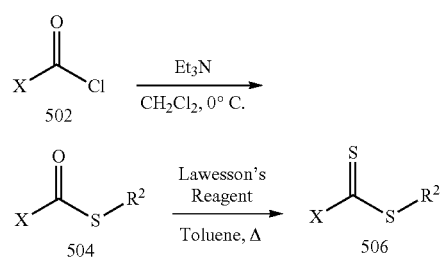

Scheme 6

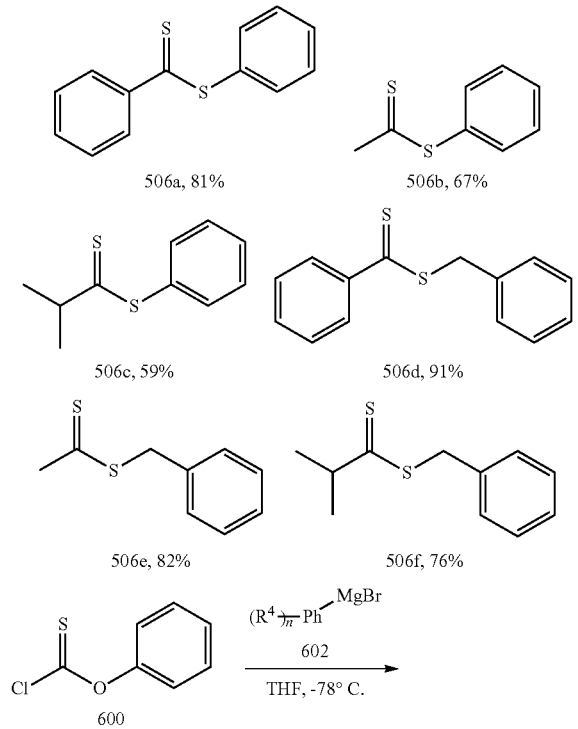

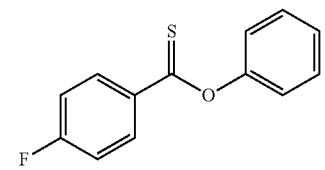

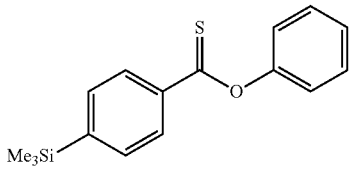

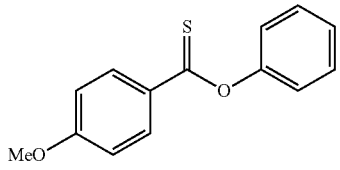

Representative method embodiments and procedures also are provided in the Examples section of the present disclosure.

V. Method of Using Donor Compound Embodiments

In embodiments described herein, the donor compound, or any composition thereof, can be used to generate $H_2S$ and thus can be used to deliver $H_2S$ to a subject or sample. In some embodiments, the donor compound can comprise a therapeutic agent and thus also can be used to deliver the therapeutic agent to a subject simultaneously (or substantially simultaneously) with $H_2S$ release. In additional embodiments, the donor compound embodiments can facilitate bioconjugation along with $H_2S$ release. The donor compound embodiments can be used in in vivo, in vitro, or ex vivo methods to increase $H_2S$ concentration and/or $H_2S$ activity in a sample or a subject and also to treat a subject by delivering a therapeutic agent to the subject.

In particular disclosed embodiments, the method can comprise exposing a subject or a sample to a donor compound embodiment or a composition thereof. In some embodiments, the method is an in vitro method and it comprises exposing a sample, such as a biological sample obtained from a subject (or other samples), to the donor compound or a composition thereof. In some embodiments, the method is an in vivo method and it comprises exposing a subject, such as a human or other animal, to the donor compound or a composition thereof (such as a pharmaceutical composition). In some embodiments, the subject or the sample can be exposed to an amount of the donor compound that is sufficient to increase the amount of $H_2S$ in the subject or sample to a certain level. For example, in subjects or samples that are determined to have deficient amounts of $H_2S$, the donor compound can be administered at a concentration sufficient to increase the $H_2S$ concentration back to a normally accepted level. What constitutes a "normally accepted level" can depend on the type of subject or sample (e.g., cell or tissue types involved), but could be determined by a person of ordinary skill in the art with the benefit of this disclosure. In some embodiments, the "normally accepted level" can exist in the nanomolar to low micromolar range.

Dosage amounts, such as therapeutically effective amounts, of the donor compound embodiments typically are selected to be amounts that will deliver $H_2S$ and/or a therapeutic agent, wherein such compounds are individually delivered in amounts ranging from greater than 0 mg/kg/day (such as 0.0001 mg/kg/day, 0.001 mg/kg/day, or 0.01 mg/kg/day) to 100 mg/kg/day. In embodiments where the donor compound is administered as a pharmaceutical composition, the amount of the donor compound in the composition can be an amount sufficient to deliver $H_2S$ and/or a therapeutic agent (individually) in amounts ranging from greater than 0 mg/kg/day (such as 0.0001 mg/kg/day, 0.001 mg/kg/day, or 0.01 mg/kg/day) to 100 mg/kg/day.

In some embodiments, the method can further comprise exposing the subject or the sample to a reactive compound that facilitates release of $H_2S$. In some embodiments, however, the reactive compound can inherently be present in the subject or the sample. In embodiments where the reactive compound is added to the subject or sample, it can be administered by any suitable means (e.g., immersing the sample in a solution comprising the reactive compound; or by oral administration, parenteral administration, or the like).

In some embodiments, the method can further comprise detecting and/or measuring a detectable signal produced after exposing the sample or the subject to the donor compound, and/or after exposing the sample or the subject to a reactive compound. In some embodiments, the detectable signal is produced by a detectable label and/or a detectable moiety. In some donor compound embodiments comprising a detectable moiety, release of a heteroatom-terminated compound from the donor compound can produce the detectable signal. In embodiments where the donor compound comprises a detectable label, the detectable signal can be produced in the sense that a biomolecule that has been labeled with the detectable label becomes detectable due to the detectable signal produced by the detectable label. In some embodiments, the biomolecule becomes labeled by forming a reactive compound conjugate, which is formed after reaction of the reactive compound and the donor compound. In yet additional embodiments, the detectable label can be a member of a specific binding pair and thus can produce a detectable signal after binding to the other member of the binding pair that itself comprises a fluorophore or other such detectable moiety or that is, itself, can produce a detectable signal. In some embodiments, detecting a detectable signal can comprise visualizing a color, fluorescent, and/or phosphorescent change in a sample (e.g., by using the naked eye or by using a fluorescent lamp). In some embodiments, detecting and/or measuring a detectable signal can comprise using a measurement technique, such as using spectroscopic methods (e.g., UV-visible spectroscopy, fluorescence spectroscopy, phosphorescence spectroscopy, or the like), a fluorescent microscope, a fluorescence scanner, or a flow cytometer to observe and/or quantify the detectable signal.

As discussed above, the donor compound embodiments described herein not only can be used to release $H_2S$, but they also can be used as a platform for biochemical labeling and/or bioconjugation. In such embodiments, the donor compound can comprise an X group (as illustrated in Formula I), wherein X is (or comprises) a detectable label, such as a fluorophore or a biochemical label, such as a member of a specific binding pair (e.g., biotin), a hapten, an antibody, or the like. Such donor compound embodiments can be reacted with a suitable reactive compound that is to be labeled. In some embodiments, the reactive compound can be (or can comprise) a peptide, an oligomer, a protein, an enzyme, or other biomolecules that have (or can be conjugated to) functional groups capable of reacting with the donor compound so as to form a reactive compound conjugate. In particular disclosed embodiments, the reactive compound conjugate can be formed between one or more functional groups of the reactive compound (or reactive compounds) and the carbon atom of the C=S group illustrated in any of the donor compound formulas provided herein.

Reactive compounds that can be used in combination with the donor compounds disclosed herein to either release $H_2S$, or to release $H_2S$ and also facilitate labeling or bioconjugation, as discussed above, typically have at least one reactive functional group that can covalently bind to the carbon atom of the C=S group illustrated in the donor compound formulas provided herein. In some embodiments, the reactive compound comprises two functional groups that each can covalently bind to the carbon atom of the C=S group illustrated in the donor compound formulas provided herein. In embodiments of reactive compounds comprising two such functional groups, the reactive compound can comprise a first functional group selected from a thiol group, a hydroxyl group, an amine group, or other nucleophilic heteroatom group; and a second functional group selected from a thiol group, a hydroxyl group, an amine group, or other nucleophilic heteroatom group. In particular disclosed embodiments, the first functional group and the second functional group can be the same or different. In some embodiments, the functional groups that react with the donor compound can belong to two separate reactive compounds. For example, one reactive compound can comprise a first functional group and another reactive compound can comprise a second functional group. In such embodiments, both reactive compounds become bound to the X group of the donor compound through the carbon atom that, in Formulas I, IIA, and IIB, is bound via a double bond to the illustrated sulfur atom.

In some embodiments wherein the first and second functional groups are part of the same reactive compound, the reactive compound can have a structure satisfying Formula III. Reactive compounds satisfying Formula III are able to react with the donor compound to release $H_2S$ from the donor compound and further form a cyclic product with the donor compound, wherein the cyclic product can have a structure satisfying Formula IV. In embodiments where the X group of Formulas I, IIA, and/or IIB is (or comprises) a detectable label and the reactive compound further comprises a biomolecule, the cyclic product formed between the donor compound and the reactive compound constitutes a reactive compound conjugate that can be detected in a sample or a subject using detection techniques described herein.

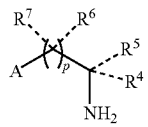

Formula III

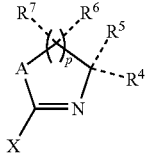

Formula IV

With reference to Formulas III and IV above, variable A can be a heteroatom (or heteroatom-containing group), such as oxygen, sulfur, or $N(R')_2$ (for Formula III) or NR' (for Formula IV), wherein each R' independently is hydrogen, aliphatic, heteroaliphatic, aromatic, or any combination thereof; each of $R^4$ and $R^5$, if present (such as when the dashed optional bond to which is each is attached is present and is a single bond), independently can be selected from aliphatic, heteroaliphatic, haloaliphatic, haloheteroaliphatic, aromatic, or any combinations thereof; each of $R^6$ and $R^7$, if present (such as when the dashed optional bond to which is each is attached is present and is a single bond), independently can be selected from aliphatic, heteroaliphatic, haloaliphatic, haloheteroaliphatic, aromatic, or any combinations thereof; and p can be an integer selected from 1 to 4, such as 1, 2, 3, or 4; and in some independent embodiments, at least one of $R^4$, $R^5$, $R^6$, or $R^7$ comprises a biomolecule, such as a protein, an antibody, an enzyme, or the like. In some such independent embodiments, at least one of $R^4$, $R^5$, $R^6$, or $R^7$ is a biomolecule or is a -linker-biomolecule group. With reference to Formula IV, X can be as recited above for Formulas I, IIA, and IIB and typically is or comprises a detectable label. In particular disclosed embodiments of Formula IV, X is a fluorophore, a -linker-fluorophore group, a biochemical label, or a -linker-biochemical label group, wherein the biochemical label can be a member of a specific binding pair (e.g., biotin), a hapten, an antibody, or the like and at least one of $R^4$, $R^5$, $R^6$, or $R^7$ can comprise a biomolecule, such as a protein, an antibody, an enzyme, or the like. In some embodiments, at least one of $R^4$, $R^5$, $R^6$, or $R^7$ is a biomolecule or is a -linker-biomolecule group. In particular disclosed embodiments, the reactive compound is (or comprises) cysteine, homocysteine, penicillamine, or the like.

Without intending to be limited to a particular theory of operation, it currently is believed that the reaction between the donor compound and the reactive compound can have a mechanism as illustrated in Scheme 7.

Scheme 7

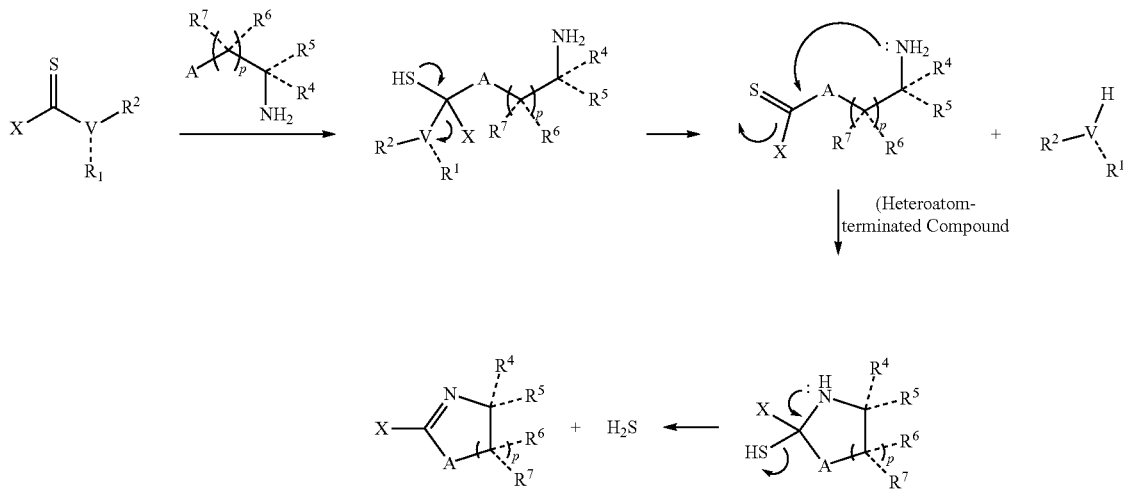

Representative embodiments may involve a mechanism as illustrated in Schemes 7A and 7B.

Scheme 7A

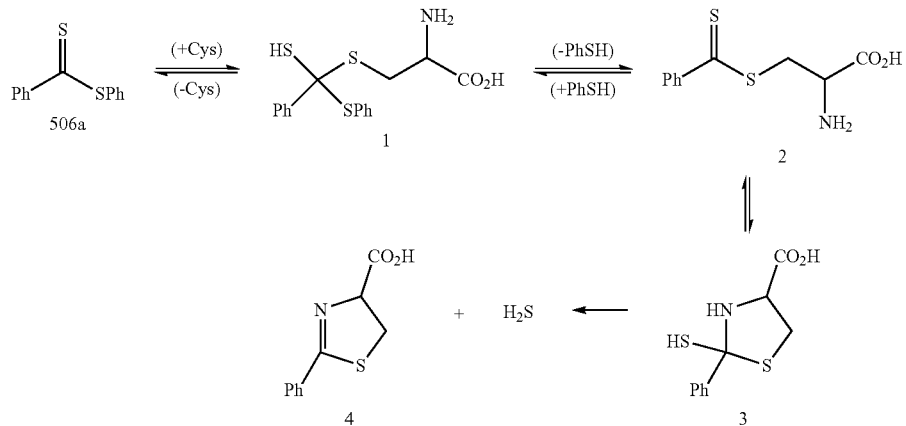

With reference to Scheme 7A, it currently is believed that initial nucleophilic attack by cysteine on compound 506a generates tetrahedral intermediate 1, which collapses upon thiocarbonyl formation and extrusion of thiophenol (a representative heteroatom-terminated compound) to yield intermediate 2. Nucleophilic attack by the pendant amine generates intermediate 3, which extrudes $H_2S$ upon formation of dihydrothiazole 4. Based on the negligible loss in $H_2S$-releasing efficiency in the presence of excess GSH, the generation of 1 and 2 is likely highly reversible and could provide enhanced selectivity of the dithioester moiety for cysteine.

be a heterocyclic group; and provided that the compound is not O-phenyl benzothioate, O-phenyl 4-methylbenzothioate, O-phenyl 4-methoxybenzothioate, or O-phenyl 4-fluorobenzothioate.

In some embodiments, X is alkyl, alkenyl, alkynyl, aryl, heteroaryl, a detectable label bound indirectly to the carbon atom of the C=S group through an aliphatic, heteroaliphatic, or aromatic linker, or any combination thereof. In some embodiments, the detectable label is biotin or a fluorophore selected from a xanthene derivative, cyanine or a cyanine derivative, a naphthalene derivative, coumarin or a coumarin derivative, an oxadiazole derivative, an anthra- Scheme 7B

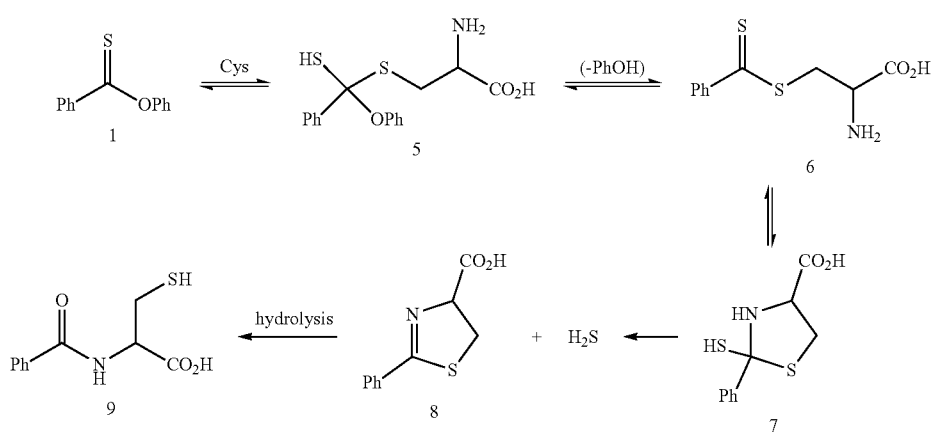

With reference to Scheme 7B, and without intending to be bound to a single theory of operation, it currently is believed that initial nucleophilic addition by cysteine on 1 generates tetrahedral intermediate 5, which collapses to form dithioester intermediate 6 and extrude one equivalent of phenol (a representative heteroatom-terminated compound). Subsequent nucleophilic attack by the pendant amine on the thiocarbonyl leads to the formation of substituted thiazolidine 7. Loss of $H_2S$, either by direct extrusion of $HS^-$ or solvent-assisted extrusion of $H_2S$, results in formation of dihydrothiazole 8, which could be further hydrolyzed to form N-benzoyl-cysteine (9).

V. Overview of Several Embodiments

Disclosed herein are embodiments of compounds having a structure satisfying Formula I

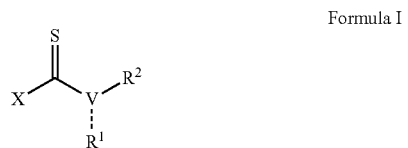

Formula I wherein: X is aliphatic, heteroaliphatic, haloaliphatic, haloheteroaliphatic, aromatic, or any combination thereof; V is a heteroatom other than nitrogen; $R^1$, if present, is hydrogen, aliphatic, haloaliphatic, haloheteroaliphatic, heteroaliphatic, aromatic, or any combination thereof; and $R^2$ is aliphatic, heteroaliphatic, haloaliphatic, haloheteroaliphatic, aromatic, or any combination thereof; or, together with $R^1$ and V, can cene derivative, a pyrene derivative, an oxazine derivative, an acridine derivative, and a tetrapyrrole derivative.

In any or all of the above embodiments, V is oxygen or sulfur.

In any or all of the above embodiments, $R^2$ is aliphatic, heteroaliphatic, aromatic, aliphatic-aromatic, heteroaliphatic-aromatic, -aromatic-$(R^3)_m$, aliphatic-aromatic-$(R^3)_m$, or heteroaliphatic-aromatic-$(R^3)_m$, wherein m can be an integer selected from 0-5 and each $R^3$ independently is aldehyde, ketone, ester, carboxylic acid, acyl, acyl halide, cyano, sulfonate, nitro, nitroso, pyridinyl, alkyl halide, halogen, haloaliphatic, ammonium, amide, alkoxy, thioether, amine, hydroxyl, thiol, ether, acyloxy, aliphatic, aryl, aliphatic-aryl, heteroaliphatic-aryl, a fluorophore, morpholine or a derivative thereof, a phosphonium or phosphine group, a an NSAID, or any combinations thereof.

In any or all of the above embodiments, the compound has a structure satisfying any one or more of Formulas IIA or IIB

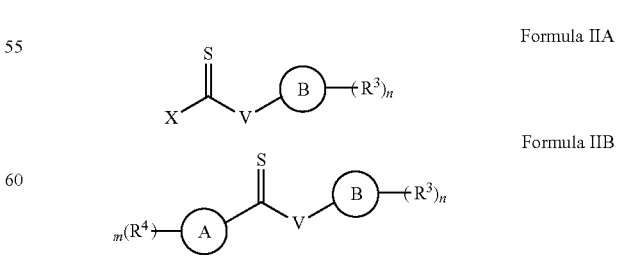

Formula IIA

Formula IIB wherein X is lower aliphatic; ring B is aromatic, aliphatic-aromatic, or heteroaliphatic-aromatic; ring A is aromatic, aliphatic-aromatic, or heteroaliphatic-aromatic; $R^3$, if present, is a substituent other than hydrogen; $R^4$, if present, is a substituent other than hydrogen; n is an integer selected from 0 to 10; and m is an integer selected from 0 to 10.

In some embodiments, each of rings A and B independently are aryl or heteroaryl.

In any or all of the above embodiments, $R^3$ and/or $R^4$ are present and $R^3$ is aldehyde, ketone, ester, carboxylic acid, acyl, acyl halide, cyano, sulfonate, nitro, nitroso, pyridinyl, alkyl halide, halogen, haloaliphatic, ammonium, amide, alkoxy, thioether, amine, hydroxyl, thiol, ether, acyloxy, aliphatic, aryl, -aliphatic-aryl, an NSAID, or any combinations thereof; and $R^4$ is aldehyde; ketone; ester; carboxylic acid; acyl; acyl halide; cyano; sulfonate; nitro; nitroso; pyridinyl; alkyl halide; halogen; haloaliphatic; ammonium; amide; alkoxy; thioether; amine; hydroxyl; thiol; ether; acyloxy; aliphatic; aryl; -aliphatic-aryl; biotin; a fluorophore; -linker-biotin or -linker-fluorophore, wherein the linker is an aliphatic or heteroaliphatic linker.

In any or all of the above embodiments, the compound has a structure satisfying any one or more of formulas IIA-IIE Formula IIIA
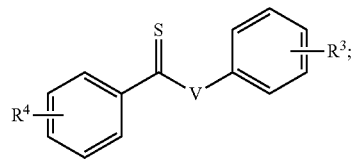

Formula IIIB
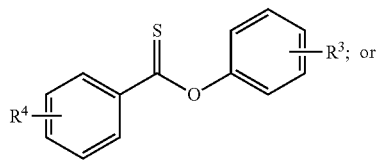

Formula IIIC
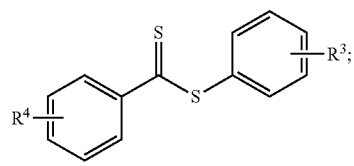

Formula IIID
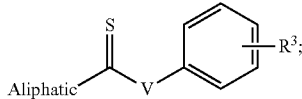

Formula IIIE
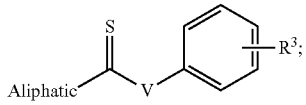

wherein each of $R^3$ and $R^4$ are present and independently are aliphatic, heteroaliphatic, haloaliphatic, haloheteroaliphatic, aromatic, or any combination thereof.

In any or all of the above embodiments, the compound has a structure satisfying any one or more of Formulas IIIA-IIIC Formula IVA
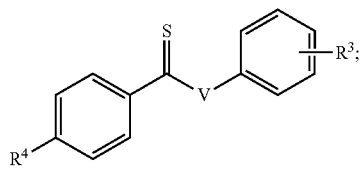

Formula IVB
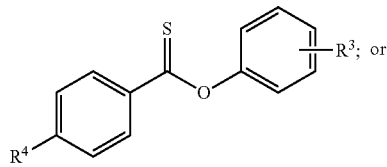

Formula IVC
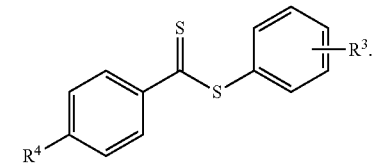

In any or all of the above embodiments, the compound has a structure satisfying any one of Formulas VA-VC Formula VA
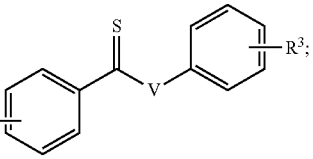

Formula VB
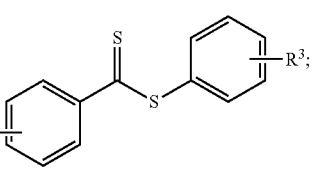

or

Formula VC
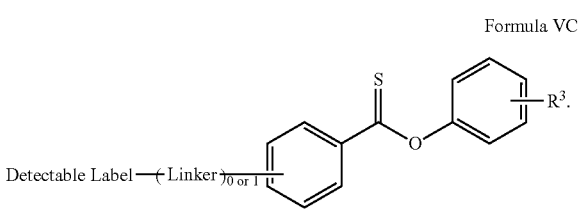

In any or all of the above embodiments, the compound has a structure satisfying any one or more of Formulas VIA-VIF Formula VIA
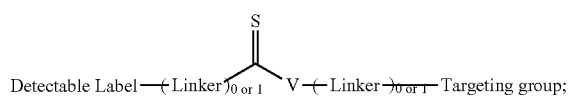

Formula VIB

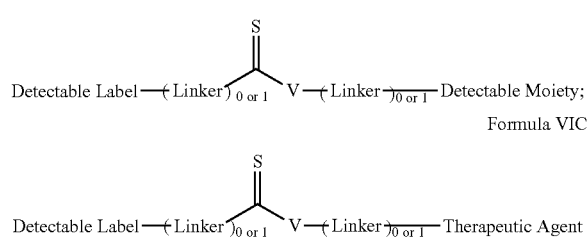

Formula VIC

Detectable Label—(Linker)₀ or ₁—V—(Linker)₀ or ₁—Therapeutic Agent wherein each linker, if present, independently is aliphatic, heteroaliphatic, or aromatic; the detectable label is biotin or a fluorophore; the detectable moiety is a fluorophore; the therapeutic agent is naproxen; and the targeting group is morpholine or a derivative thereof, a phosphonium group, a phosphine group, or a quaternary amine.

In any or all of the above embodiments, the compound is selected from any of the particular species described herein.

Also disclosed herein are embodiments of a pharmaceutical composition, comprising a compound according to any or all of the above compound embodiments, and a pharmaceutically acceptable excipient.

Also disclosed herein are embodiments of a method, comprising exposing a cell sample, a tissue sample, a bodily fluid sample, or a subject to a compound according to claim 1, or a pharmaceutical composition thereof. In some embodiments, the compound comprises a first member of a specific binding pair and the method further comprises exposing the sample or the subject to a second member of the specific binding pair.

In any or all of the above embodiments, the method further comprises analyzing the sample or the subject to detect a reaction between the compound and a reactive component that is inherently present in the subject or the sample or that is added to the subject or the sample, wherein the reaction produces a detectable signal, $H_2S$, or a combination thereof.

In some embodiments, analyzing comprises detecting and/or measuring a color change, a fluorescence change, or a change in concentration of $H_2S$ or any combination thereof.

In any or all of the above embodiments, the method further comprises measuring an amount of $H_2S$ released from the compound.

In any or all of the above embodiments, the subject has or is at risk of developing a disease associated with $H_2S$ deficiency or $H_2S$ misregulation and/or a disease associated with carbonic anhydrase overexpression.

In any or all of the above embodiments, the disease is a cardiovascular disease selected from heart failure, myocardial reperfusion injury, atherosclerosis, hypertension, hypertrophy, or any combinations thereof; diabetes; inflammation; a neurological disease; cancer; a disease involving insufficient wound healing; erectile dysfunction; or any combinations thereof.

VI. Examples

Reagents were purchased from Sigma-Aldrich, Tokyo Chemical Industry (TCI) or VWR and used directly as received. S-Phenyl benzothioate was synthesized according to the procedure disclosed in *Eur. J. Org. Chem.* 2015, 2015, 4840-4842, the relevant portion of which is incorporated herein by reference. N-phenylthiobenzamide was synthesized according to the procedure disclosed in *J. Am. Chem. Soc.* 2015, 137, 9273-9280, the relevant portion of which is incorporated herein by reference. Methyl 2-phenyl-4,5-dihydrothiazole-4-carboxylate (CysDHT) was synthesized according to the procedure described in *J. Org. Chem.* 2006, 71, 8276-8278, the relevant portion of which is incorporated herein by reference. Deuterated solvents were purchased from Cambridge Isotope Laboratories and used as received. $^1H$ and $^{13}C\{^1H\}$ NMR spectra were recorded on a Bruker 500 MHz instrument. Chemical shifts are reported relative to residual protic solvent resonances. Silica gel (SiliaFlash F60, Silicycle, 230-400 mesh) was used for column chromatography. All air-free manipulations were performed under an inert atmosphere using standard Schlenk technique or an Innovative Atmospheres $N_2$-filled glove box. UV-Vis spectra were acquired on an Agilent Cary 60 UV-Vis spectrophotometer equipped with a Quantum Northwest TC-1 temperature controller at 25° C.±0.05° C.

$H_2S$ Detection Materials and Methods—Phosphate buffered saline (PBS) tablets (1×, CalBioChem) were used to prepare buffered solutions (140 mM NaCl, 3 mM KCl, 10 mM phosphate, pH 7.4) in deionized water. Buffer solutions were sparged with $N_2$ to remove dissolved oxygen and stored in an $N_2$-filled glovebox. Donor stock solutions (in DMSO) were prepared inside an $N_2$-filled glovebox and stored at −25° C. until immediately before use. Trigger stock solutions (in PBS) were freshly prepared in an $N_2$-filled glovebox immediately before use.

General Procedure for Measuring $H_2S$ Release via Methylene Blue Assay (MBA)—Scintillation vials containing 20 mL of PBS were prepared in an $N_2$-filled glovebox. To these solutions, 20 µL of 500 mM analyte stock solution (in PBS) was added for a final concentration of 500 µM. While stirring, the solutions were allowed to thermally equilibrate in heating block at the desired temperature for approximately 20-30 minutes. Immediately prior to donor addition, 0.5 mL solution of the methylene blue cocktail were prepared in disposable 1.5 mL cuvettes. The methylene blue cocktail solution contained: 200 µL of 30 mM $FeCl_3$ in 1.2 M HCl, 200 µL of 20 mM N,N-dimethyl-p-phenylene diamine in 7.2 M HCl, and 100 µL of 1% (w/v) $Zn(OAc)_2$. To begin an experiment, 20 µL of 25 mM donor stock solution (in DMSO) was added for a final concentration of 25 µM. At set time points after the addition of donor, 500 µL reaction aliquots were added to the methylene blue cocktail solutions and incubated for 1 hour at room temperature shielded from light. Absorbance values at 670 nm were measured 1 hour after addition of reaction aliquot. Each experiment was performed in quadruplicate unless stated otherwise.

MBA Calibration Curve—Solutions containing 0.5 mL of the methylene blue cocktail and 0.5 mL PBS containing 500 µM cysteine were freshly prepared in disposable cuvettes (1.5 mL). Under inert conditions, a 10 mM stock solution of NaSH (Strem Chemicals) in PBS was prepared and diluted to 1 mM. Immediately after dilution, 1 mM NaSH was added to 1.0 mL solutions for final concentrations of 10, 20, 30, 40, and 50 µM. Solutions were mixed thoroughly, incubated at room temperature for 1 hour, and shielded from light. Absorbance values at 670 nm were measured after 1 hour.

Computational Details and Geometries—Structures were initially constructed in Avogadro and optimized using the UFF force field. These resultant structures were then further geometrically optimized using a hybrid GGA functional, B3LYP, with a large triple zeta basis, 6-311++G**, that includes diffuse and polarization functions for all atoms. A pseudosolvent polarizable continuum model was used (water), to partially account for solvent stabilization. VeryTight convergence criteria for forces and displacements, as implemented in Gaussian 09. Energetics were compared to a double zeta basis, 6-31+G*, which showed similar trends and energies.

Transition states were located using i) a potential energy surface scan with the modredundant feature to locate a good starting point for ii) a transition state search. The transition states were confirmed using vibrational analysis as evidenced by a single imaginary frequency corresponding to the direction of bond making/breaking.

Example 1

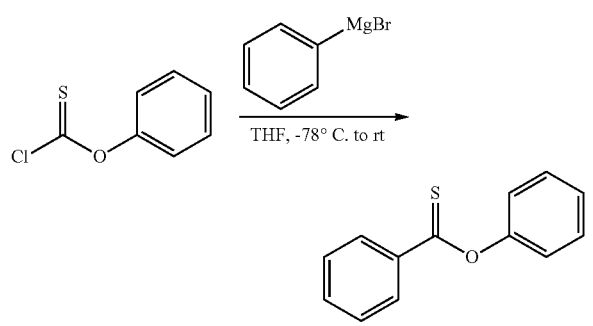

O-Phenyl benzothioate (compound 604a) was made as follows: Phenyl chlorothionoformate (14.8 mmol, 1.1 equivalents) was added to anhydrous THF (20 mL) at −78° C. under $N_2$. While stirring, phenylmagnesium bromide (12.8 mmol, 1.0 M in THF, 1.0 equivalents) was added dropwise, and the reaction solution was stirred for 1 hour at −78° C. After 1 hour, the reaction solution was allowed to warm to room temperature and stirred for an additional 2 hours. The reaction was then quenched by addition of deionized $H_2O$ (30 mL) and extracted with $CH_2Cl_2$ (3×30 mL). The combined organic extractions were washed with brine (30 mL), and dried over $MgSO_4$. After filtration, the solvent was removed under reduced pressure, and the desired product purified by column chromatography (10% $CH_2Cl_2$ in hexanes, $R_f$=0.33). The resultant product was isolated as a bright orange-yellow liquid. 938 mg (34%).

$^1$H NMR (500 MHz, $CDCl_3$) δ: 8.37 (d, J=7.3 Hz, 2H), 7.63 (t, J=7.5 Hz, 1H), 7.48 (q, J=7.2 Hz, 4H), 7.33 (t, J=7.4 Hz, 1H), 7.14 (d, J=7.5 Hz, 2H). $^{13}$C{$^1$H} NMR (126 MHz, $CDCl_3$) δ: 211.22, 155.03, 138.11, 133.46, 129.76, 129.44, 128.42, 126.53, 122.31. HRMS-EI$^+$ (m/z): [M+H]$^+$ calcd for $C_{13}H_{10}OS$, 214.04524; found, 214.04478.

HPLC analysis was performed on an Agilent 1260 HPLC instrument with a Poroshell 120 EC-C18 4.6×100 mm column and monitored at 280 nm. Solvent A: 95% $H_2O$, 5% MeOH, Solvent B: 100% MeCN. Gradient: 35% Solvent A/65% Solvent B for 2 minutes. Change to 100% Solvent B over 4 min and hold for 6.5 minutes. Change to 35% Solvent A/65% Solvent B over 0.5 min and hold for 4.5 minutes. Flow Rate: 0.5 mL/min, 24 injection.

Other compound embodiments were made according to the representative method described below (and also as summarized in Scheme 8 below).

Scheme 8

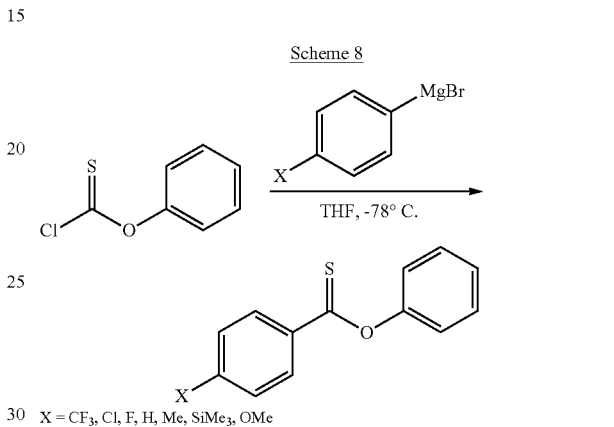

X = $CF_3$, Cl, F, H, Me, $SiMe_3$, OMe

To an oven-dried round bottom flask containing 5 mL of anhydrous THF, activated Mg turnings (1.0 equiv) and a functionalized bromobenzene (1.0 equivalents) were added. The solution is heated to reflux for 1 hour to generate the corresponding Grignard reagent. In a separate, oven-dried round bottom flask, phenyl chlorothionoformate (1.0 equivalents) is dissolved in 20 mL anhydrous THF and cooled to −78° C. The generated Grignard reagent is cooled to room temperature and added dropwise to the cooled solution of phenyl chlorothionoformate. The reaction is stirred for 1 hour at −78° C., then allowed to warm to room temperature for 1 hour. The reaction is subjected to an aqueous workup and the crude product is purified by column chromatography to afford the desired donor compound embodiment. Yields and spectroscopic data are provided in Table 1.

TABLE 1

| Product | Yield (%) | Characterization Data |
| --- | --- | --- |
| Compound 604b (F$_3$C-C$_6$H$_4$-C(=S)-O-C$_6$H$_5$) | 12 | $^1$H NMR (500 MHz, CDCl$_3$) δ 8.45 (d, J = 8.2 Hz, 2 H), 7.73 (d, J = 8.3 Hz, 2 H), 7.49 (t, J = 8.0 Hz, 2 H), 7.35 (t, J = 7.5 Hz, 1 H), 7.14 (d, J = 7.5 Hz, 2 H). $^{19}$F NMR (471 MHz, CDCl$_3$) δ −63.08. $^{13}$C NMR (126 MHz, CDCl$_3$) δ 209.20, 154.81, 140.58, 134.47 (q, J = 32.7 Hz), 129.91, 129.65, 126.82, 125.45 (q, J = 3.8 Hz), 123.90 (q, J = 272.8 Hz), 122.13. HRMS-EI+ (m/z): [M + H]$^+$ calcd for C$_{14}$H$_9$F$_3$OS, 282.03263; found, 282.03300. |

TABLE 1-continued

| Product | Yield (%) | Characterization Data |
|---|---|---|
| 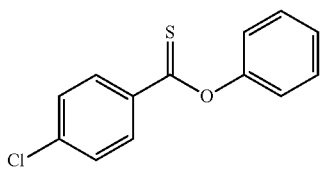 [SMILES: S=C(Oc1ccccc1)c1ccc(Cl)cc1] Compound 604c | 13 | $^1$H NMR (500 MHz, CDCl$_3$) δ 8.30 (d, J = 8.6 Hz, 2 H), 7.48 (t, J = 8.0 Hz, 2 H), 7.43 (d, J = 8.5 Hz, 2 H), 7.33 (t, J = 7.7 Hz, 1 H), 7.12 (d, J = 8.4 Hz, 2 H). $^{13}$C NMR (126 MHz, CDCl$_3$) δ 209.55, 154.87, 140.17, 136.43, 130.73, 129.82, 128.70, 126.67, 122.23. TOF MS-EI+ (m/z): [M + H]$^+$ calcd for C$_{13}$H$_9$ClOS, 248.0063; found, 248.0063. |
| 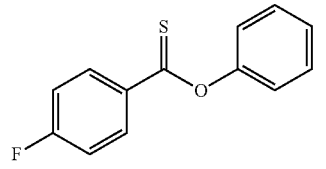 [SMILES: Fc1ccc(C(=S)Oc2ccccc2)cc1] Compound 604d | 35 | $^1$H NMR (500 MHz, CDCl$_3$) δ 8.40 (dd, J = 9.0, 5.5 Hz, 2 H), 7.50-7.45 (m, 2 H), 7.37-7.31 (m, 1 H), 7.13 (t, J = 8.6 Hz, 4 H). $^{19}$F NMR (471 MHz, CDCl$_3$) δ −105.08 (p, J = 7.1 Hz). $^{13}$C NMR (126 MHz, CDCl$_3$) δ 209.49, 166.36 (d, J = 256.1 Hz), 154.90, 134.52 (d, J = 3.2 Hz), 132.04 (d, J = 9.2 Hz), 129.78, 126.61, 122.27, 115.51 (d, J = 21.8 Hz). HRMS-EI+ (m/z): [M + H]$^+$ calcd for C$_{13}$H$_9$FOS, 232.03467; found, 232.03542. |
| 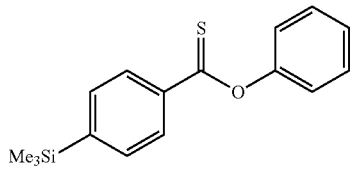 [SMILES: C[Si](C)(C)c1ccc(C(=S)Oc2ccccc2)cc1] Compound 604e | 4 | $^1$H NMR (500 MHz, CDCl$_3$) δ 8.31 (d, J = 8.1 Hz, 2 H), 7.62 (d, J = 6.4 Hz, 2 H), 7.48 (t, J = 7.9 Hz, 2 H), 7.33 (t, J = 7.2 Hz, 1 H), 7.13 (d, J = 6.9 Hz, 2 H), 0.32 (s, 9 H). $^{13}$C NMR (126 MHz, CDCl$_3$) δ 211.43, 155.04, 147.77, 138.20, 133.37, 129.76, 128.27, 126.51, 122.33, −1.19. |
| 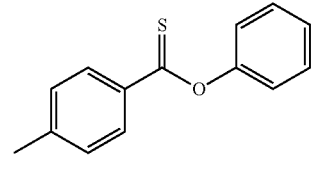 [SMILES: Cc1ccc(C(=S)Oc2ccccc2)cc1] Compound 604f | 6 | $^1$H NMR (500 MHz, CDCl$_3$) δ 8.27 (d, J = 8.4 Hz, 1 H), 7.47 (dd, J = 8.4, 7.4 Hz, 2 H), 7.35-7.29 (m, 1 H), 7.26 (t, J = 4.1 Hz, 2 H), 7.13 (d, J = 7.4 Hz, 2 H), 2.43 (s, 3 H). $^{13}$C NMR (126 MHz, CDCl$_3$) δ 211.14, 155.05, 144.56, 135.74, 129.71, 129.57, 129.14, 126.44, 122.38, 21.87. HRMS-EI+ (m/z): [M + H]$^+$ calcd for C$_{14}$H$_{12}$OS, 228.06089; found, 228.06155. |
| 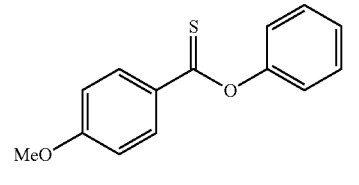 [SMILES: COc1ccc(C(=S)Oc2ccccc2)cc1] Compound 604g | 7 | $^1$H NMR (500 MHz, CDCl$_3$) δ 8.36 (d, J = 9.0 Hz, 2 H), 7.46 (dd, J = 8.5, 7.5 Hz, 2 H), 7.35-7.28 (m, 1 H), 7.12 (dd, J = 8.6, 1.1 Hz, 2 H), 6.94 (d, J = 9.0 Hz, 2 H), 3.91 (s, 3 H). $^{13}$C NMR (126 MHz, CDCl$_3$) δ 210.19, 164.30, 155.06, 131.86, 131.35, 129.67, 126.39, 122.47, 113.63, 55.76. HRMS-EI+ (m/z): [M + H]$^+$ calcd for C$_{14}$H$_{12}$O$_2$S, 244.05580; found, 244.05548. |

Example 2

Scheme 9

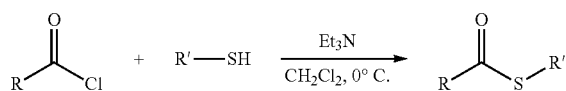

In this example, compounds were made using the method outlined in Schemes 9 (above) and 10 (see below). The desired thiol (1.1 equivalents) and triethylamine (1.1 equivalents) were added to anhydrous CH$_2$Cl$_2$ (20 mL) and cooled to 0° C. Once cooled, the desired acid chloride (1.0 equivalents) was added dropwise, and the reaction was stirred at 0° C. for 1 hour. The reaction was quenched with deionized H$_2$O (30 mL), and the organic layer was separated. The aqueous layer was extracted with CH$_2$Cl$_2$ (2×20 mL) and the combined organic extractions were washed with brine (1×20 mL), dried over MgSO$_4$, and concentrated under reduced pressured. The desired product was purified by column chromatography. Yields and characterization data for particular compounds is provided below

TABLE 2

| Product | Yield (%) | Characterization Data |
|---|---|---|
| 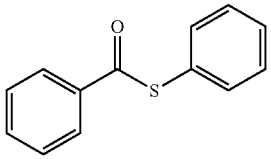 | 96 | $R_f$ = 0.23 (25% CH$_2$Cl$_2$ in hexanes)<br>$^1$H NMR (600 MHz, CDCl$_3$) δ: 8.04 (d, 2H), 7.61 (t, 1H), 7.55-7.44 (m, 7H).<br>$^{13}$C{$^1$H} NMR (151 MHz, CDCl$_3$) δ: 190.14, 136.63, 135.09, 133.65, 129.52, 129.24, 128.74, 127.48, 127.34.<br>TOF MS (ASAP$^+$) (m/z): [M + H]$^+$ calc'd for C$_{13}$H$_{10}$OS 215.0531; found 215.0548 |
| 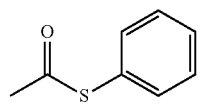 | 86 | $R_f$ = 0.42 (50% CH$_2$Cl$_2$ in hexanes)<br>$^1$H NMR (500 MHz, CDCl$_3$) δ: 7.42 (s, 5H), 2.43 (s, 3H).<br>$^{13}$C{$^1$H} NMR (151 MHz, CDCl$_3$) δ: 194.06, 134.44, 129.43, 129.19, 127.91, 30.19.<br>TOF MS (ASAP$^+$) (m/z): [M + H]$^+$ calc'd for C$_8$H$_8$OS 153.0374; found 153.0374 |
| 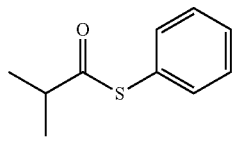 | 66 | $R_f$ = 0.56 (50% CH$_2$Cl$_2$ in hexanes)<br>$^1$H NMR (500 MHz, CDCl$_3$) δ: 7.41 (s, 5H), 2.87 (hept, J = 6.9, 1.9 Hz, 1H), 1.27 (d, J = 7.0, 1.8 Hz, 6H).<br>$^{13}$C NMR (126 MHz, CDCl$_3$) δ: 201.85, 134.56, 129.17, 129.09, 127.87, 42.99, 19.37.<br>TOF MS (ASAP$^+$) (m/z): [M + H]$^+$ calc'd for C$_{10}$H$_{12}$OS 181.0687; found 181.0705 |
| 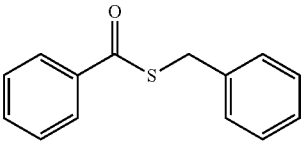 [SMILES: O=C(SCc1ccccc1)c1ccccc1] | 93 | $R_f$ = 0.40 (33% CH$_2$Cl$_2$ in hexanes)<br>$^1$H NMR (500 MHz, CDCl$_3$) δ: 7.98 (d, J = 7.6 Hz, 2H), 7.57 (t, J = 7.4 Hz, 1H), 7.45 (t, J = 8.0 Hz, 2H), 7.39 (d, J = 8.1 Hz, 2H), 7.33 (t, J = 7.5 Hz, 2H), 7.29-7.24 (m, 1H), 4.33 (s, 2H).<br>$^{13}$C NMR (126 MHz, CDCl$_3$) δ: 191.27, 137.45, 136.78, 133.42, 128.96, 128.61, 127.31, 127.28, 33.32. |
| 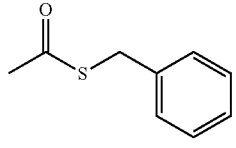 | 67 | $R_f$ = 0.24 (25% CH$_2$Cl$_2$ in hexanes)<br>$^1$H NMR (600 MHz, CDCl$_3$) δ: 7.31-7.27 (m, 4H), 7.27-7.23 (m, 1H), 4.13 (s, 2H), 2.35 (s, 3H).<br>$^{13}$C NMR (151 MHz, CDCl$_3$) δ: 195.09, 137.56, 128.77, 128.60, 127.24, 33.42, 30.29.<br>TOF MS (ASAP$^+$) (m/z): [M + Na]$^+$ calc'd for C$_9$H$_{10}$OS 189.0350; found 189.0485 |
| 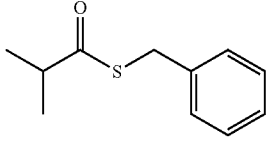 | 66 | $R_f$ = 0.48 (33% CH$_2$Cl$_2$ in hexanes)<br>$^1$H NMR (600 MHz, CDCl$_3$) δ: 7.31-7.28 (m, 4H), 7.25-7.22 (m, 1H), 4.11 (s, 2H), 2.76 (hept, J = 6.9 Hz, 1H), 1.21 (d, J = 6.9 Hz, 6H).<br>$^{13}$C NMR (151 MHz, CDCl$_3$) δ: 203.44, 137.73, 128.79, 128.59, 127.17, 42.88, 32.89, 19.35.<br>TOF MS (ASAP$^+$) (m/z): [M + H]$^+$ calc'd for C$_{11}$H$_{14}$OS 195.0844; found 195.0835 |

Scheme 10

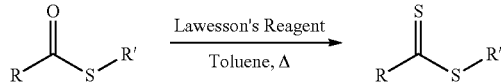

Next, the desired thioester (1.0 equivalents) and Lawesson's Reagent (0.75 equivalents) were added to anhydrous toluene (20 mL) and heated to 120° C. under reflux. After 5.5 h, the reaction mixture was cooled to room temperature and filtered. The filtrate was concentrated under reduced pressure, and the desired product purified by column chromatography.

TABLE 3

| Product | Yield (%) | Characterization Data |
|---|---|---|
| 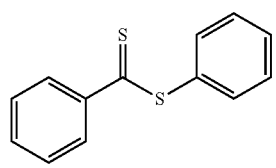 [SMILES: S=C(Sc1ccccc1)c1ccccc1]<br>Compound 506a | 81 | $R_f$ = 0.42 (20% CH$_2$Cl$_2$ in hexanes)<br>$^1$H NMR (600 MHz, CDCl$_3$) δ: 8.10 (d, J = 7.1 Hz, 1H), 7.57 (t, 1H), 7.54-7.47 (m, 6H), 7.45-7.40 (m, 2H).<br>$^{13}$C NMR (151 MHz, CDCl$_3$) δ: 228.49, 144.59, 135.38, 132.60, 131.38, 130.36, 129.66, 128.40, 126.99.<br>TOF MS (ASAP$^+$) (m/z): [M + H]$^+$ calc'd for C$_{13}$H$_{10}$S$_2$ 231.0302; found 231.0302 |

TABLE 3-continued

| Product | Yield (%) | Characterization Data |
|---|---|---|
| 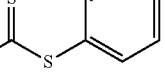 Compound 506b | 67 | $R_f = 0.40$ (20% $CH_2Cl_2$ in hexanes)<br>$^1H$ NMR (500 MHz, $CDCl_3$) δ: 7.52-7.46 (m, 3H), 7.45-7.40 (m, 2H), 2.87 (s, 3H).<br>$^{13}C$ NMR (151 MHz, $CDCl_3$) δ: 234.30, 134.74, 131.77, 130.36, 129.60, 38.95.<br>TOF MS (ASAP$^+$) (m/z): [M + H]$^+$ calc'd for $C_8H_8S_2$ 169.0146; found 169.0132 |
| 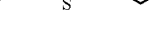 Compound 506c | 59 | $R_f = 0.58$ (25% $CH_2Cl_2$ in hexanes)<br>$^1H$ NMR (600 MHz, $CDCl_3$) δ: 7.50-7.47 (m, 3H), 7.42-7.39 (m, 2H), 3.54 (hept, J = 6.7 Hz, 1H), 1.38 (d, J = 6.6 Hz, 6H).<br>$^{13}C$ NMR (151 MHz, $CDCl_3$) δ: 246.77, 134.97, 130.83, 130.18, 129.51, 48.70, 24.24.<br>TOF MS (ASAP$^+$) (m/z): [M + H]$^+$ calc'd for $C_{10}H_{12}S_2$ 197.0459; found 197.0463 |
|  Compound 506d | 91 | $R_f = 0.41$ (20% $CH_2Cl_2$ in hexanes)<br>$^1H$ NMR (500 MHz, $CDCl_3$) δ: 8.00 (d, J = 7.7 Hz, 2H), 7.53 (t, J = 7.5 Hz, 1H), 7.42-7.27 (m, 8H), 4.61 (s, 2H).<br>$^{13}C\{^1H\}$ NMR (126 MHz, $CDCl_3$) δ: 227.69, 144.75, 134.97, 132.40, 129.29, 128.72, 128.34, 127.75, 126.90, 42.28.<br>TOF MS (ASAP$^+$) (m/z): [M + H]$^+$ calc'd for $C_{14}H_{12}S_2$ 245.0459; found 245.0471 |
|  Compound 506e | 82 | $R_f = 0.54$ (25% $CH_2Cl_2$ in hexanes)<br>$^1H$ NMR (600 MHz, $CDCl_3$) δ: 7.34-7.26 (m, 5H), 4.46 (s, 2H), 2.85 (s, 3H).<br>$^{13}C\{^1H\}$ NMR (151 MHz, $CDCl_3$) δ: 232.29, 135.13, 129.09, 128.67, 127.66, 41.98, 38.85.<br>TOF MS (ASAP$^+$) (m/z): [M + Na]$^+$ calc'd for $C_9H_{10}S_2$ 183.0302; found 183.0281 |
| 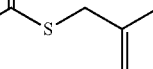 Compound 506f | 76 | $R_f = 0.58$ (25% $CH_2Cl_2$ in hexanes)<br>$^1H$ NMR (600 MHz, $CDCl_3$) δ: 7.34-7.26 (m, 5H), 4.45 (s, 2H), 3.42 (hept, J = 6.7 Hz, 1H), 1.34 (d, J = 6.7 Hz, 7H).<br>$^{13}C\{^1H\}$ NMR (151 MHz, $CDCl_3$) δ: 245.91, 135.22, 129.13, 128.67, 127.58, 49.35, 40.52, 24.19.<br>TOF MS (ASAP$^+$) (m/z): [M + H]$^+$ calc'd for $C_{11}H_{14}S_2$ 211.0615; found 211.0612 |

Example 3

Figure 2:
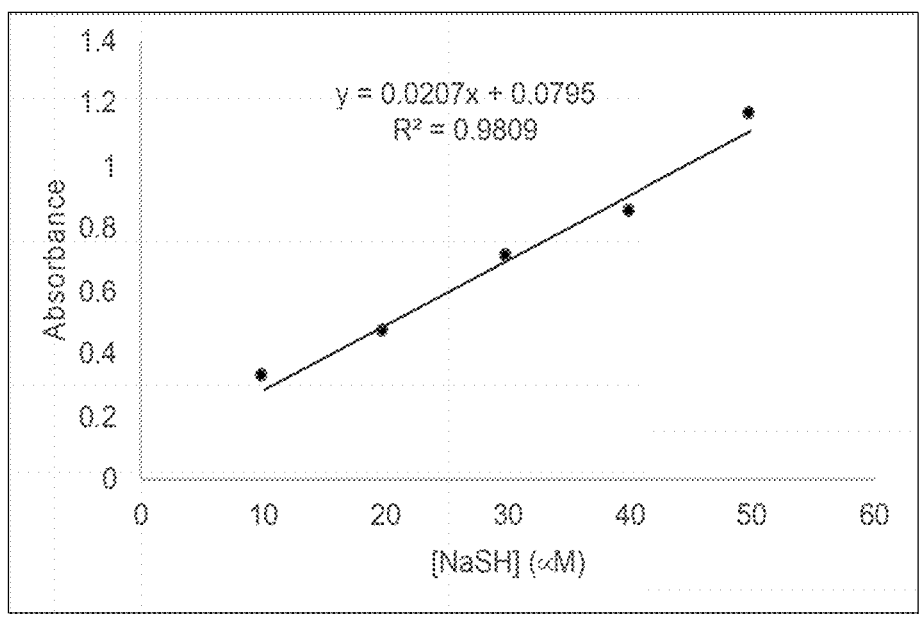
FIG. 2 is a methylene blue assay (MBA) calibration curve generated using 500 μM NaSH.
Figure 3:
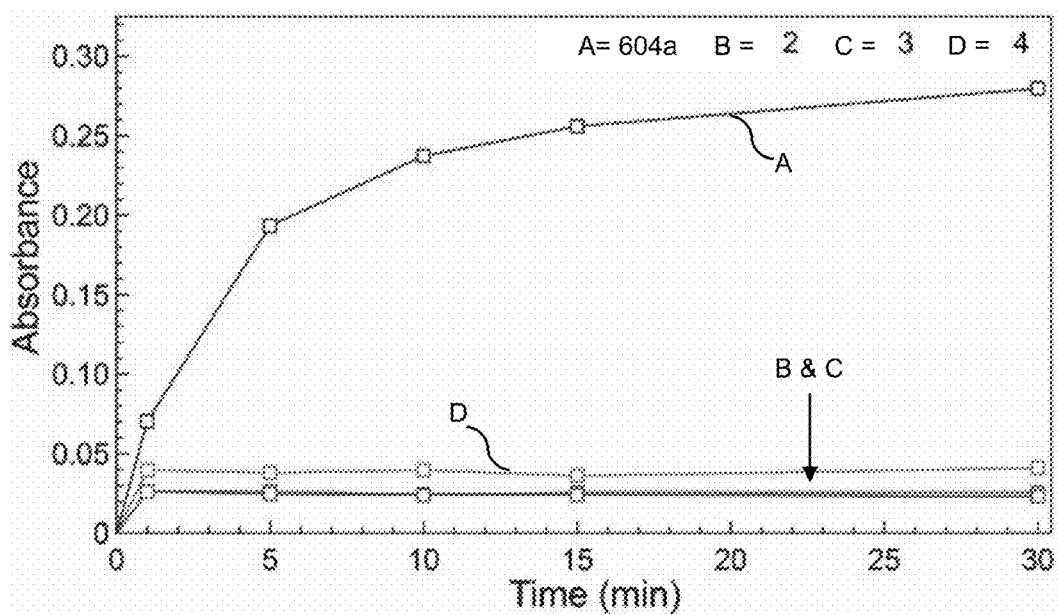
FIG. 3 is a graph showing lack of $H_2S$ release from phenyl benzoate (2), S-phenyl benzothioate (3), and N-phenylbenzamide (4), as compared to compound 604a in the presence of cysteine (500 μM, 20 equiv.)

In this example, the release rate of $H_2S$ from a representative donor compound (a thionoester compound) was evaluated at various concentrations of cysteine (25-500 μM). In this example, the compound released $H_2S$ at faster rates in the presence of excess cysteine, an exemplary reactive compound. As shown in FIG. 1, increasing the concentration of cysteine results in a dose-dependent increase in the $H_2S$ release rate. In this example, the released $H_2S$ was measured and quantified using the methylene blue assay for $H_2S$. In a typical use of this assay, aliquots from a reaction mixture with the $H_2S$ donor and cysteine are treated with 0.5 mL of a methylene blue assay mixture containing 0.1 mL zinc acetate (1% w/v), 0.2 mL $FeCl_3$ (30 mM in 1.2 M HCl), and 0.2 mL N,N-dimethyl-p-phenylene diamine (20 mM in 7.2 M HCl)). After incubation for 1 hour, the absorbance at 670 nm is measured and converted to a $H_2S$ concentration by using the $H_2S$ calibration curve. To assess the $H_2S$-releasing efficiency from the compound embodiments, a methylene blue calibration curve was used to quantify the $H_2S$ release (FIG. 2). It was determined that 20 μM of $H_2S$ was released from a 25 μM solution of compound 604a in the presence of 500 μM cysteine (20 equivalents), which corresponds to a releasing efficiency of 80%. In addition to compound 604a $H_2S$ release from structurally-related phenyl benzoate (2 in FIG. 3) and S-phenyl benzothioate (3 in FIG. 3) was evaluated under similar conditions. Results are shown in FIG. 3. Neither of these compounds released $H_2S$ when treated with excess cysteine. Similarly, a representative secondary thioamide, N-phenylbenzamide (4 in FIG. 3) failed to release $H_2S$ in the presence of cysteine. Without being limited to a single theory, it currently is believed that these results show that the release of $H_2S$ occurs from the thionoester moiety in the presence of cysteine.

Scheme 11

Reaction Product Analysis

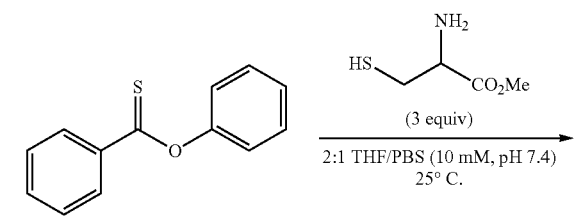

-continued

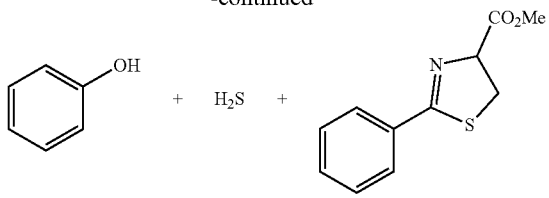

Compound 604a (0.39 mmol, 1.0 equivalents) was dissolved in 15 mL of 2:1 THF/PBS (10 mM, pH 7.4). L-cysteine methyl ester hydrochloride (1.17 mmol, 3.0 equivalents) was added in a single portion and stirred at room temperature for 2 hours. The reaction mixture was diluted with deionized $H_2O$ (~20 mL) and extracted with $CH_2Cl_2$ (3×20 mL). The combined organic extracts were washed with brine and dried over $MgSO_4$. After filtration, the solvent was removed under reduced pressure, and the purified by preparative thin layer chromatography (1:1 $CH_2Cl_2$ in hexanes). Compound 604a $R_f$=0.75 (63.6 mg, 76%) and CysDHT $R_f$=0.03 (11.0 mg, 13%) were isolated and characterized by $^1H$ and $^{13}C\{^1H\}$ NMR spectroscopy. The significant recovery of compound 604a is likely due to the lack of buffering capacity in the preparative-scale reaction.

Scheme 12

Reaction Product Analysis via HPLC

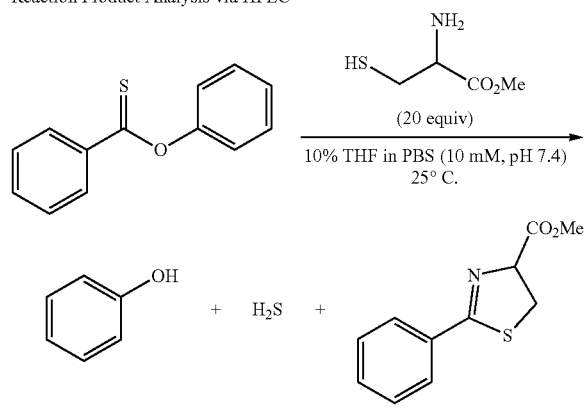

Figure 4:
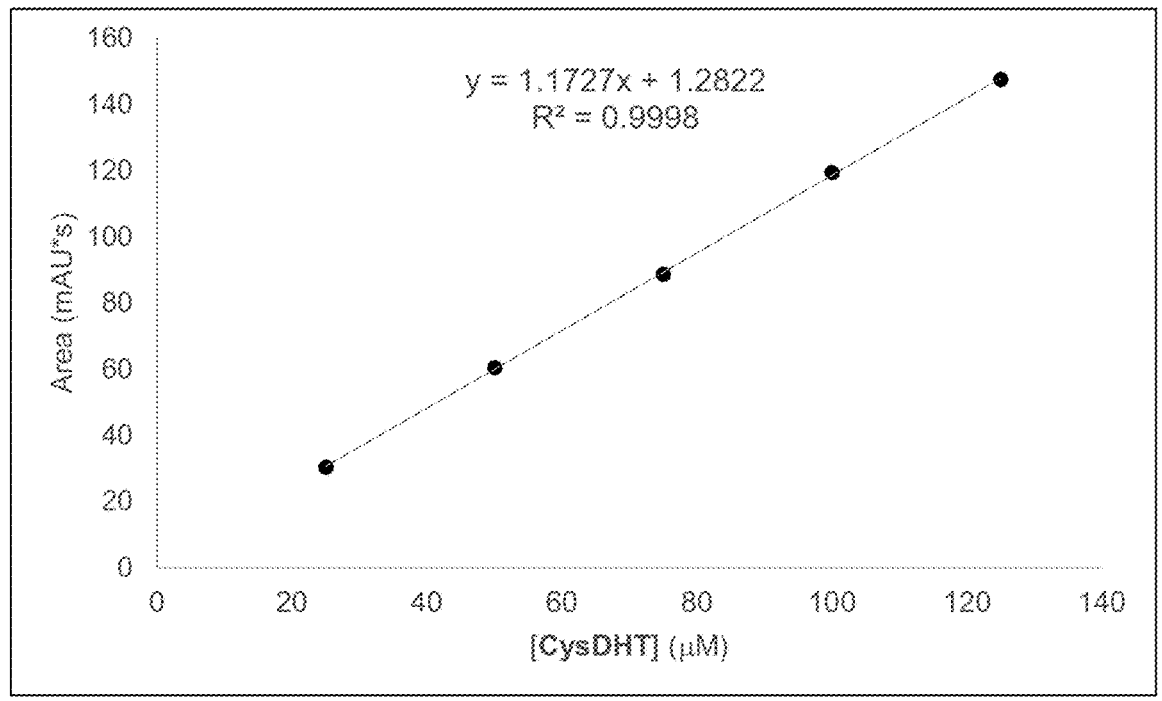
FIG. 4 is an HPLC calibration curve of CysDHT.

To a 20 mL solution of 10% THF in PBS (10 mM, pH 7.4) containing 2 mM L-cysteine methyl ester (20 equivalents), 20 µL of 100 mM compound 604a in THF was added and stirred at room temperature. After 1 hour, a 1 mL reaction aliquot was analyzed by HPLC. HPLC analysis was performed on an Agilent 1260 HPLC instrument with a Poroshell 120 EC-C18 4.6×100 mm column and monitored at 280 nm. Solvent A: 95% $H_2O$, 5% MeOH, Solvent B: 100% MeCN. Gradient: 35% Solvent A/65% Solvent B for 2 minutes. Change to 100% Solvent B over 4 min and hold for 6.5 minutes. Change to 35% Solvent A/65% Solvent B over 0.5 min and hold for 4.5 minutes. Flow Rate: 0.5 mL/min, 4 µL injection. The concentration of CysDHT and phenol present at the end of the reaction were determined by measurement against calibration curves for each compound (see FIG. 4).

These data confirm the release of $H_2S$ from donor compounds described herein in the presence of cysteine and demonstrates the dependence on cysteine concentrations for $H_2S$ Example 4

Figure 5:
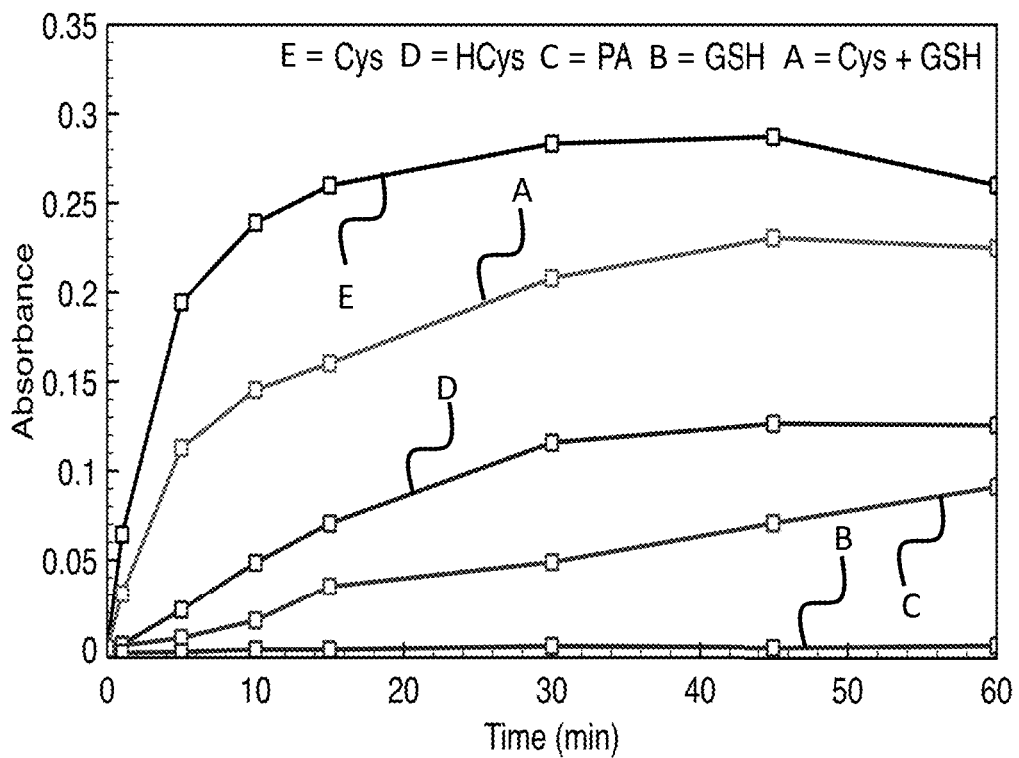
FIG. 5 is a plot showing the increased absorbance in an $H_2S$-responsive methylene blue assay when 25 μM of compound 604a is treated with 500 μM of various thiols including cysteine (Cys), homocysteine (HCys), penicillamine (PA), glutathione (GSH), and a mixture of Cys and GSH.

In addition to cysteine, donor compounds of the present disclosure can be triggered to release $H_2S$ with other reactive compounds that have pendant amino groups. To demonstrate this reactivity with different reactive compounds, solutions containing 25 µM of compound 604a (see Table 1) were treated with 500 µM of biologically relevant thiols and $H_2S$ release was measured by the spectrophotometric methylene blue assay. Results are illustrated in FIG. 5.

Treatment of compound 604a with cysteine (Cys), homocysteine (HCys) and penicillamine (PA) all result in $H_2S$ release. Treatment with glutathione (GSH), however, does not result in $H_2S$ release. Co-incubation with Cys and GSH results in $H_2S$ release, albeit at a slower rate than with Cys alone. This observation is consistent with the proposed mechanism of release and confirms that reactive components with a pendant nucleophile can promote $H_2S$ release. Additionally, a depressed rate of release was observed implying the reversibility of the reaction between a first functional group of the reactive compound and donor compound embodiments. The addition of GSH into compound 604a leads to the formation of a dithioester lacking a pendant nucleophile. Without intending to be limited to a particular theory, it currently is believed that this observation implies L-cysteine can react with donor compound embodiments to form an active intermediate for $H_2S$ release.

Example 5

Figure 6:
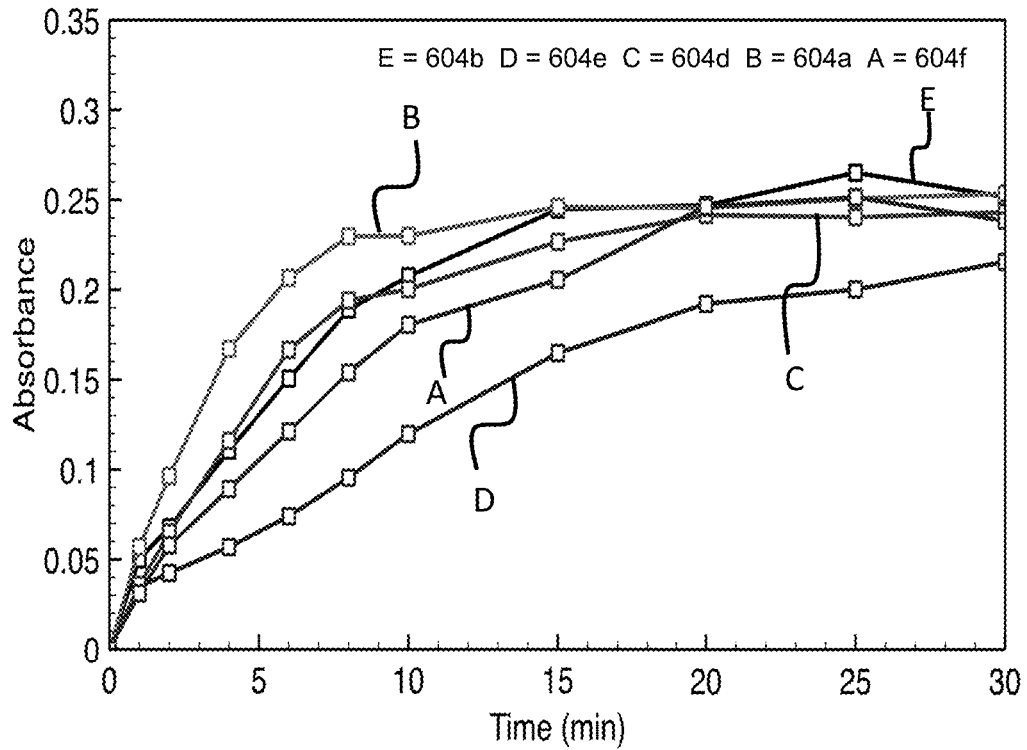
FIG. 6 is a plot showing the increased absorbance in an $H_2S$-responsive methylene blue assay when 25 μM of compounds 604a, 604b, 604c, 604d and 604f are treated with 500 μM of Cys.

In this example, the rate of $H_2S$ release from donor compound embodiments was examined by modifying the electronic substitution of X groups (as illustrated in Formula I), wherein X is a phenyl ring. For example, introduction of electron-withdrawing and electron-donating substituents to the para position of representative donor compound embodiments (e.g., diphenyl-based thionoesters) alters the rate of $H_2S$ release relative to the unfunctionalized donor compound (FIG. 6). Both electron-withdrawing and electron-donating substituents depress the rate of $H_2S$ release with electron-donating groups (e.g. -Me) having the most pronounced effect. This example demonstrates the ability to tune the rate of $H_2S$ release from donor compound embodiments by altering the electronic effects of the donor compound embodiments.

Figure 7:
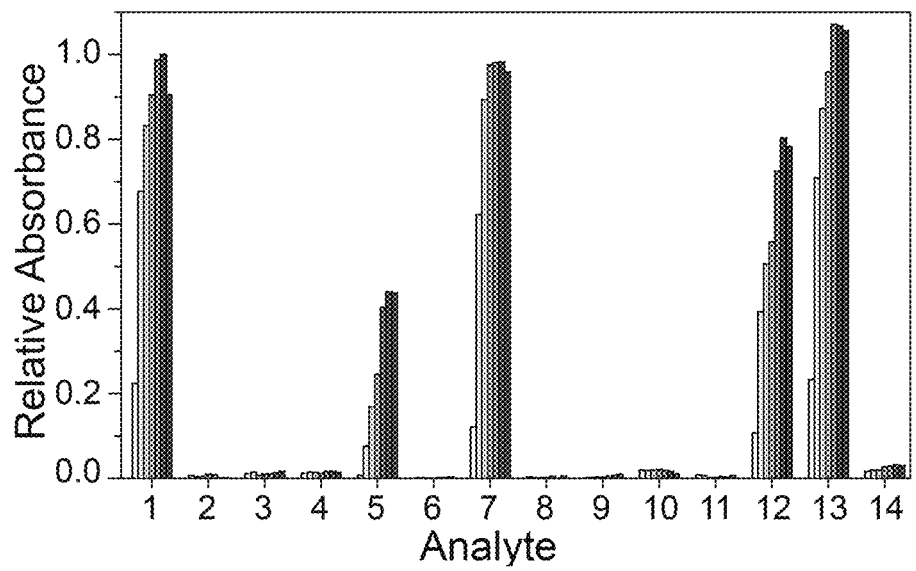
FIG. 7 is a bar graph showing results from determining the selectivity of $H_2S$ release from compound 604a in the presence of different analytes, wherein data were acquired at 1, 5, 10, 15, 30, 45, and 60 minutes and methylene blue absorbance values are relative to the maximum absorbance value obtained from $H_2S$ release in the presence of cysteine.

In this example, the selectivity of $H_2S$ release from disclosed compound embodiments was evaluated. Compound 604a was treated with biologically-relevant nucleophiles and the results are shown in FIG. 7. In particular, compound 604a was treated with: cysteine (FIG. 7, bar 1); $H_2O$ (FIG. 7, bar 2), serine (FIG. 7, bar 3), lysine (FIG. 7, bar 4), L-homocysteine (FIG. 7, bar 5), DL-penicillamine (FIG. 7, bar 6), L-cysteine methyl ester hydrochloride (FIG. 7, bar 7), N-acetyl-L-cysteine (FIG. 7, bar 8), N-acetyl-L-cysteine methyl ester (FIG. 7, bar 9), S-methyl-L-cysteine (FIG. 7, bar 10), GSH (FIG. 7, bar 11), cysteine+GSH (FIG. 7, bar 12), cysteine+lysine (FIG. 7, bar 13), PLE (1.0 U/mL) (FIG. 7, bar 14). In the absence of any added nucleophiles, no hydrolysis-mediated $H_2S$ release was observed from compound 604a at physiological pH, which was surprising as it has been shown in the art that thionoesters are hydrolyzed under basic conditions to afford the corresponding thioacid and alcohol. Also, treatment of compound 604a with serine or lysine, chosen as representative alcohol- and amine-based nucleophiles respectively, did not result in $H_2S$ release, although it has been shown in the art that amines can react with thionoesters to yield thioamides via displacement of the corresponding alcohols. To investigate this potential side reactivity, cysteine-triggered (500 μM) $H_2S$ release from compound 604a (25 μM) was measured in the presence of lysine (500 μM) and no change in $H_2S$ releasing-efficiency was observed. The reactivity of compound 604a with thiol-based nucleophiles also was investigated as shown in FIG. 7. Treatment of compound 604a with homocysteine also resulted in $H_2S$ release, although at a slower rate than from treatment with cysteine. This observation is consistent with a larger, less favorable transition state required for an intramolecular S to N acyl transfer in the homocysteine system in comparison with the cysteine system. Alternatively, the reduced rate may be reflective of the significant $pK_a$ difference between cysteine ($pK_a$~8.5) and homocysteine ($pK_a$~10),[41] meaning that under physiological conditions, the effective concentration of cysteine thiolate is much greater than homocysteine thiolate (~10% vs. ~0.03%).

It was also evaluated whether different cysteine derivatives could generate $H_2S$ release from compound 604a. Treatment of compound 604a with cysteine methyl ester did not affect $H_2S$ production, suggesting that the carboxylic acid is not required for $H_2S$ generation. By contrast, treatment of compound 604a with N-acetylcysteine, N-acetylcysteine methyl ester, or S-methylcysteine did not, in $H_2S$ release, highlighting the requirement of a 2-aminoethanethiol moiety for productive $H_2S$ release. Consistent with these results, treatment of compound 604a with GSH, the most abundant biological thiol, did not generate $H_2S$, which is consistent with some embodiments having a pendant amine to generate $H_2S$ release. Despite the lack of $H_2S$ release, GSH could still attack compound 604a to form an intermediate dithioester, which should still be sufficiently electrophilic to react with cysteine to generate $H_2S$; therefore, to evaluate if this was feasible, compound 604a (25 μM) was treated with GSH (1 mM) and cysteine (500 μM), and a reduced rate of $H_2S$ release was observed. These results suggest that the competitive, non-productive, addition of GSH to the thionoester is reversible, and that the thionoester moiety can still react with Cys in the presence of GSH to release $H_2S$. Additionally, in some embodiments, compound 604a was treated with porcine liver esterase (PLE), but $H_2S$ generation was not observed; however, consumption of the thionoester moiety by PLE or other native enzymes was not ruled out. These data demonstrate the high selectivity of the thionoester moiety towards cysteine and homocysteine for $H_2S$ release.

Example 6

Figure 8A:
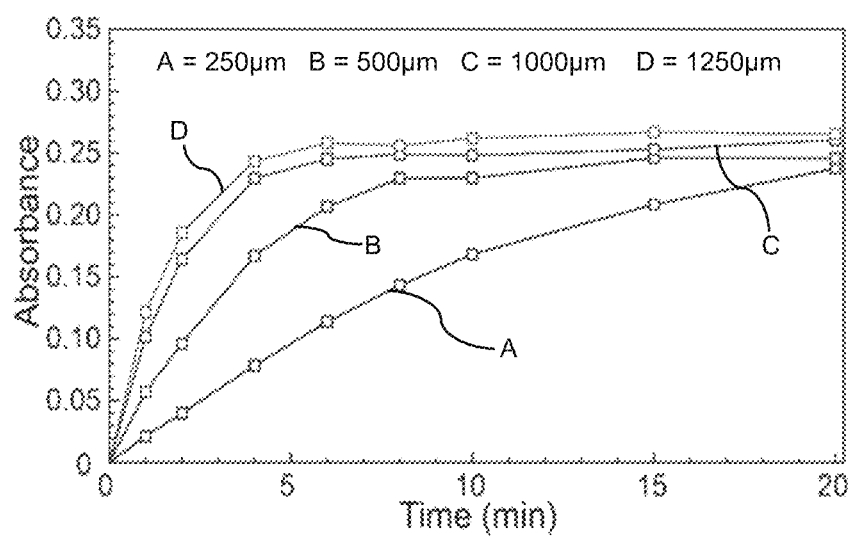
Figure 8B:
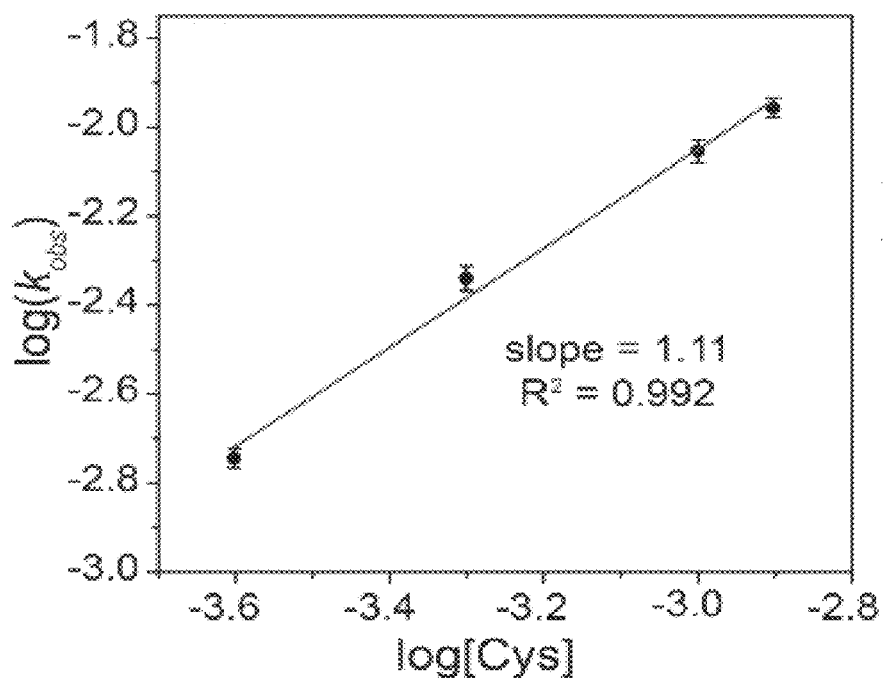
Figure 8C:
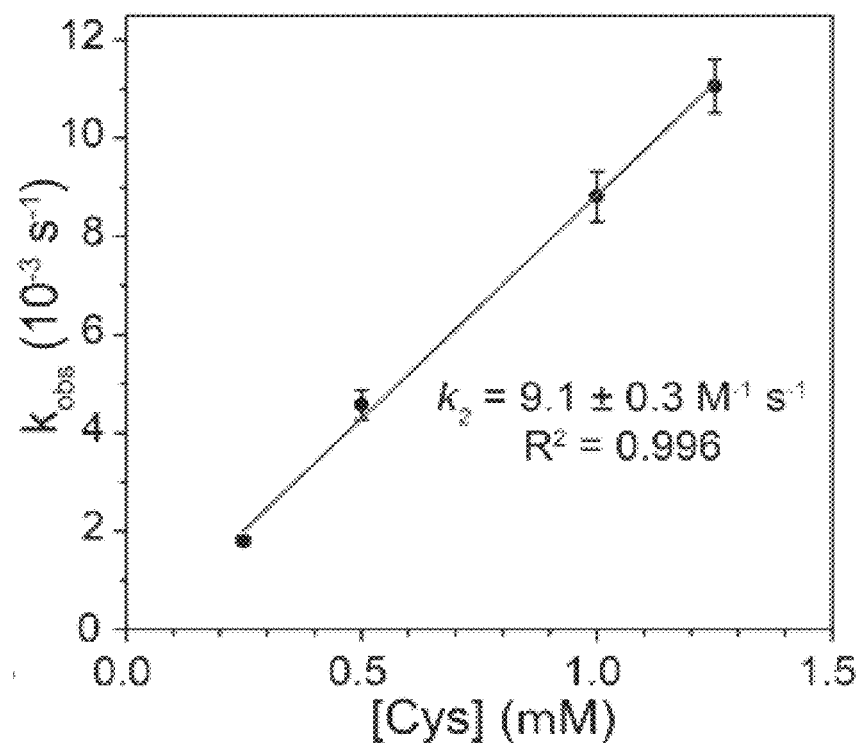

In this example, the mechanism proposed in Scheme 7B was evaluated. First, reaction order in cysteine was determined by treating compound 604a (25 μM) with varying concentrations of cysteine under pseudo-first order conditions at 25° C. and measuring $H_2S$ release using the methylene blue assay. Results are shown in FIGS. 8A-8C. Increased cysteine concentrations led to increased rates of $H_2S$ production. The resultant releasing curves were fit to obtain pseudo first-order rate constants ($k_{obs}$), and plotting log[Cys] versus log[$k_{obs}$] confirmed a first-order dependence in cysteine, which is consistent with the proposed mechanism. Additionally, the obtained $k_{obs}$ values were plotted against Cys concentrations to obtain a second-order rate constant of 9.1±0.3 $M^{-1}$ $s^{-1}$ for the reaction. In comparison to other known reactivities, the rate of cysteine-triggered $H_2S$ release from compound 604a is comparable to the rate (10-100 $M^{-1}$ $s^{-1}$) of copper (I)-catalyzed azide-alkyne cycloadditions (CuAAC), a classic example of a "click reaction."

Next, the rate-determining step in cysteine-triggered release of $H_2S$ from thionoesters was investigated. In native chemical ligation, the initial nucleophilic attack by thiols to form intermediate thioesters is reversible and has been utilized to enhance the reactivity of alkyl thioesters for native chemical ligation. However, in the presence of cysteine, the transthioesterification resulting from nucleophilic attack of the sulfhydryl group on the thioester is thought to be rate-limiting due to the rapid, and irreversible subsequent S to N acyl transfer to form the more thermodynamically-stable amide bond. In the thionoester system, the initial attack by a thiol on compound 604a results in extrusion of phenol, which is a much weaker nucleophile than a thiol and should not attack the generated dithioester intermediate. If other thiols are present in solution, then it is likely that they could attack the dithioester intermediate in a transdithioesterification reaction. This thiol exchange is supported by the observed reduced rate of $H_2S$ generation from compound 604a in the presence of competing thiols, suggesting that the initial nucleophilic attack on dithioesters is reversible.

Figure 9A:
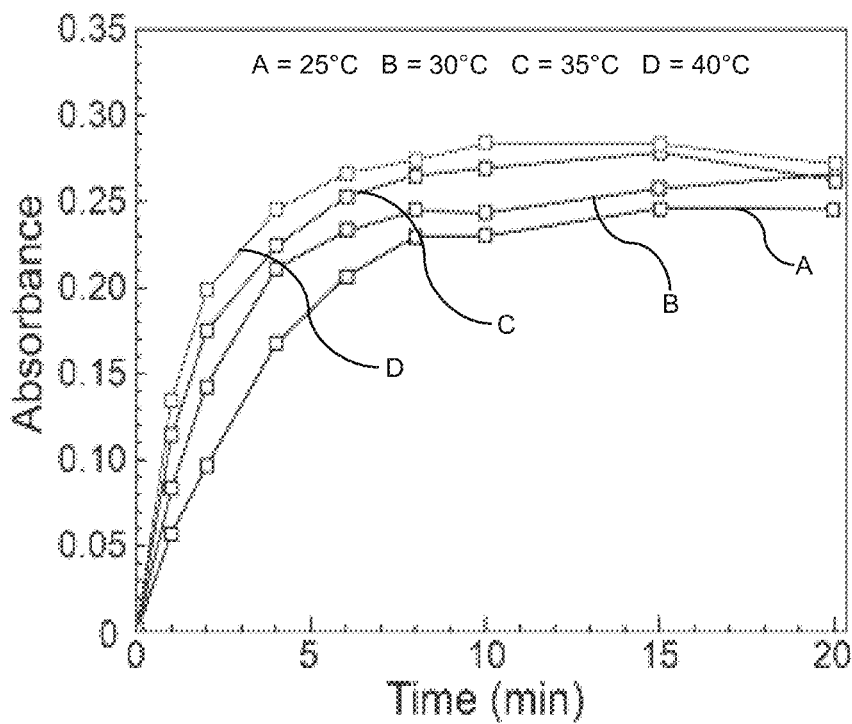
FIGS. 9A and 9B show results from analyzing the effect of temperature on rate of $H_2S$ release from compound 604a (25 μM) in the presence of cysteine (500 μM, 20 equivalents) (FIG. 9A) and Eyring analysis of $H_2S$ release from compound 604a (FIG. 9B).
Figure 9B:
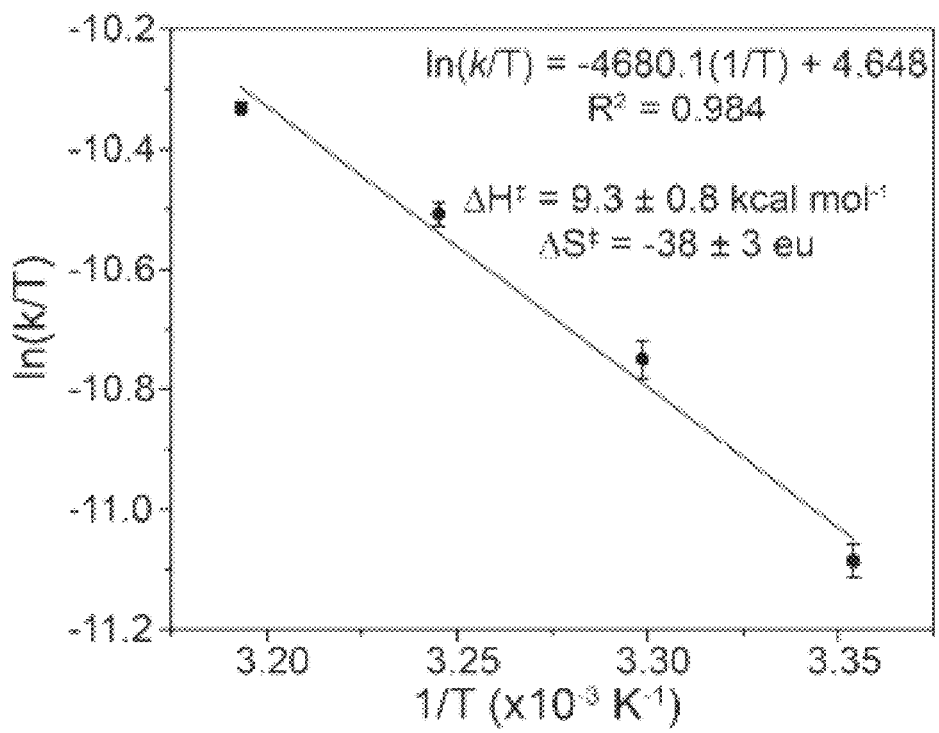

Using similar pseudo first-order conditions as those used for the cysteine order dependence investigations (25 μM compound 604a, 500 μM cysteine), an Eyring analysis was performed to determine the activation parameters for the reaction in an effort to further understand the amount of disorder in the rate-limiting transition state for the reaction (FIGS. 9A and 9B). If initial thiol addition is the rate limiting step, then a negative entropy of activation ($\Delta S^{\ddagger}$) of approximately −20 e.u., which is typical for a bimolecular reaction, should be observed. In contrast, if the intramolecular S to N thioacyl transfer to form the substituted thiazolidine is the rate limiting step then a larger, more negative $\Delta S^{\ddagger}$, likely would be observed due to the highly-ordered structure required for the intramolecular cyclization. In this example, a $\Delta S^{\ddagger}$=−38±3 eu, was observed, which is most consistent with intramolecular cyclization being the rate-determining step of the reaction.

Figure 10:
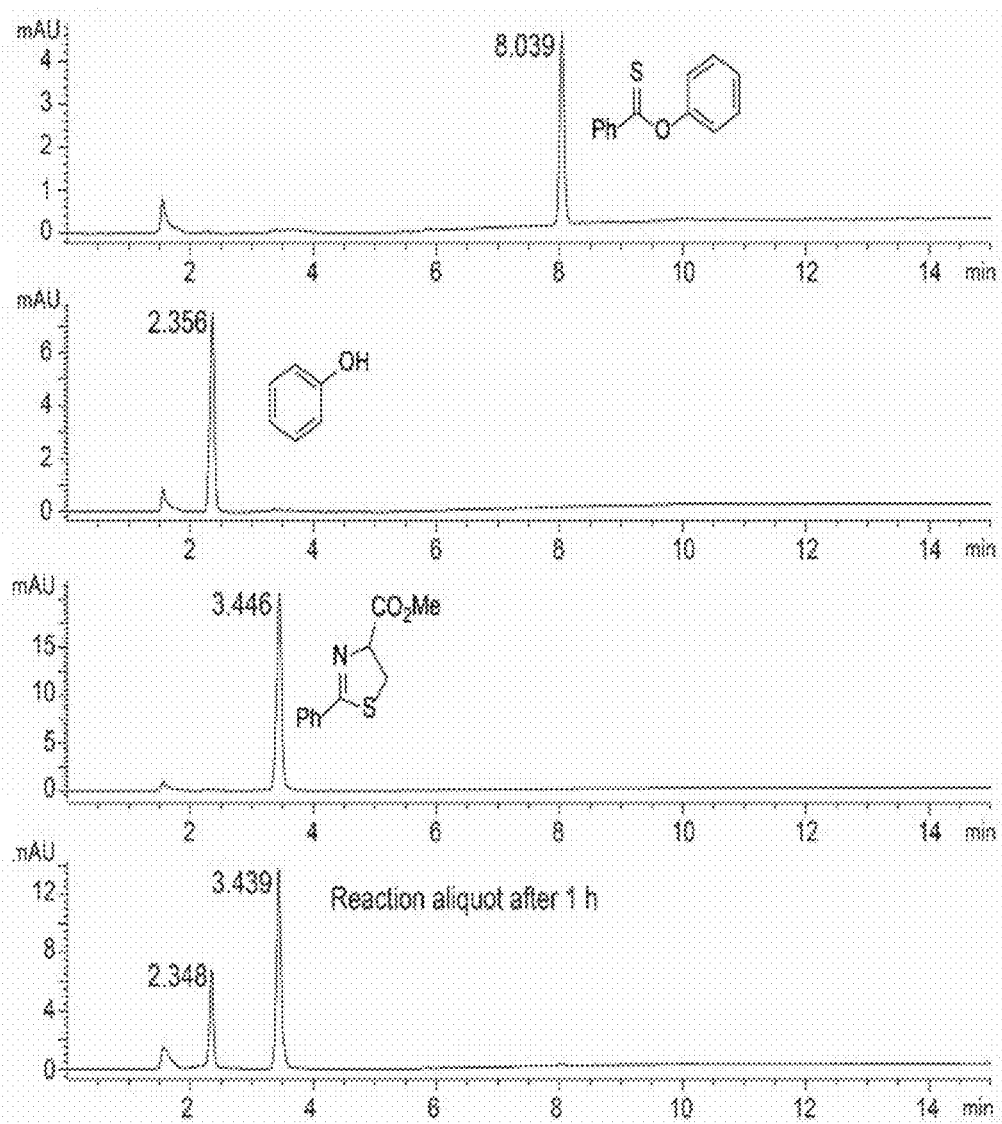
FIG. 10 is a combined HPLC trace providing HPLC traces for reaction products under the following reaction conditions: 100 μM compound 604a in PBS (10 mM, pH 7.4) with 10% THF (top trace); 100 μM PhOH in PBS (10 mM, pH 7.4) with 10% THF (second trace from top); 100 μM CysDHT in PBS (10 mM, pH 7.4) with 10% THF (second trace from bottom); and a reaction aliquot after 1 hour (bottom trace).

As a final step of characterizing the proposed mechanism, a preparative scale reaction was performed and the reaction products were isolated. In addition to recovered starting material, a cysteine-derived dihydrothiazole (CysDHT), rather than N-benzoyl-L-cysteine, was isolated as the major product of the reaction (FIG. 10). These results suggest that the dihydrothiazole is stable under aqueous conditions and is not further hydrolyzed to N-benzoyl-L-cysteine. To further confirm the formation of CysDHT from compound 604a, an authentic sample of CysDHT was synthesized and HPLC was used to monitor the reaction progress. A 100 μM solution of compound 604a was treated with 20 equivalents of cysteine and nearly complete conversion to phenol and CysDHT was observed within 1 hour. Using known concentrations of phenol and CysDHT to construct an HPLC calibration curve, the concentrations of phenol and CysDHT after 1 hour were measured to be approximately 76 μM and 64 μM, respectively, which supports the high $H_2S$-releasing efficiency of thionoesters.

Example 7

Figure 11A:
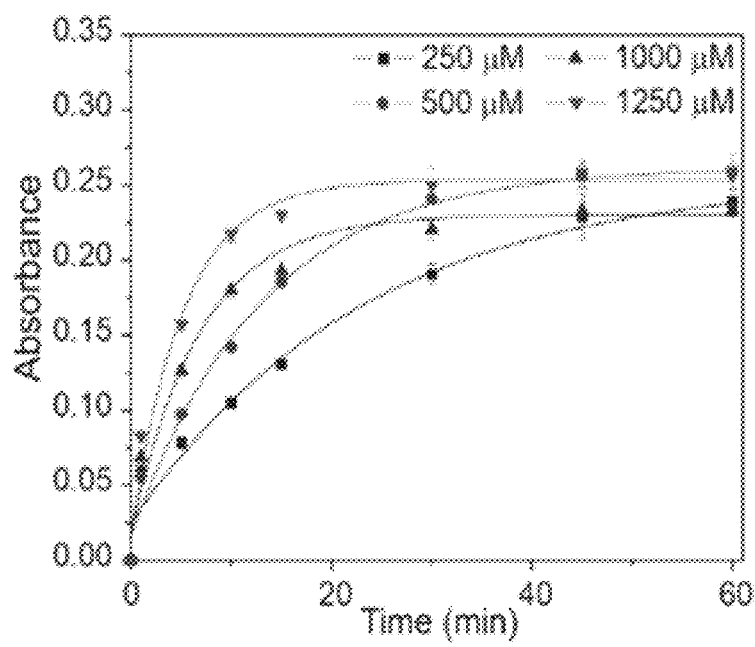
Figure 11B:
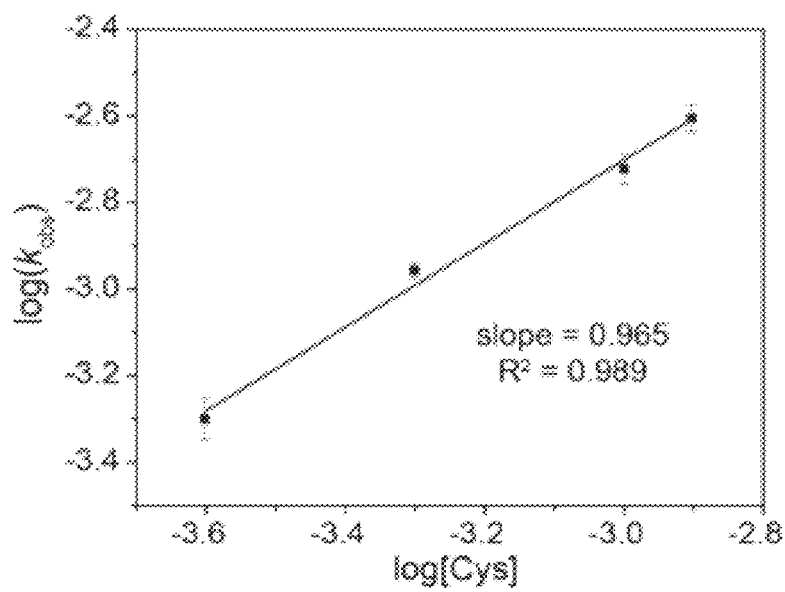
Figure 11C:
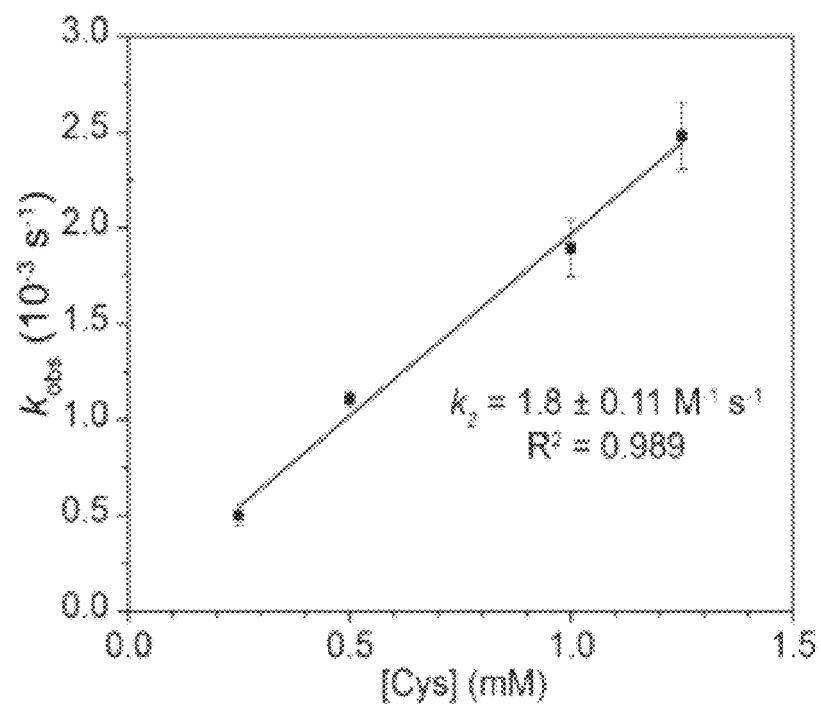

In this example the reactivity of compound 506a (25 μM)—selected as a representative dithioester compound embodiment—towards various concentrations of cysteine (250, 500, 1000, and 1250 μM) was evaluated and the release of $H_2S$ was measured via the spectrophotometric methylene blue assay, which allows for H$_2$S quantification (FIG. 11A). Increasing amounts of H$_2$S released with increasing cysteine concentrations from compound 506a. To quantify the H$_2$S-releasing efficiency, a methylene blue calibration curve was generated with NaSH and it was found that 25 μM compound 506a released approximately 17 μM H$_2$S after 1 hour, which corresponds to a releasing efficiency of ~68%. To quantify the rate of H$_2$S release, the releasing curves were fitted and pseudo-first order rate constants (k$_{obs}$) were obtained. A plot of log[Cys] versus log(k$_{obs}$) provided a linear plot with slope near one, which suggests the overall reaction is first order in cysteine and proceeds via a mechanism similar to the reaction of thionoester compound embodiments with cysteine (FIG. 11B). A plot of [Cys] versus k$_{obs}$ yielded a second-order rate constant (k$_2$) of 1.8±0.1 M$^{-1}$ s$^{-1}$ (FIG. 11C).

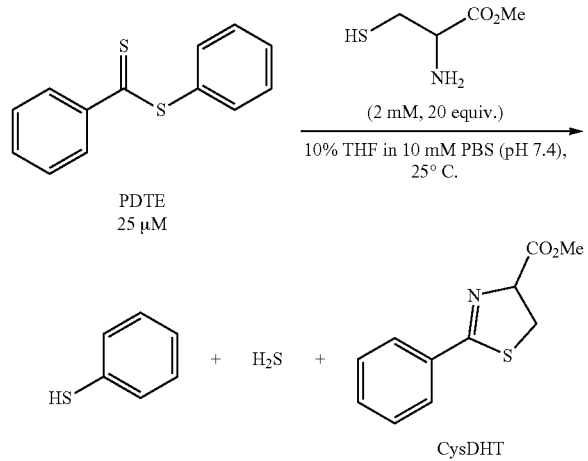

Scheme 13

Reaction Product Analysis via HPLC

Figure 12:
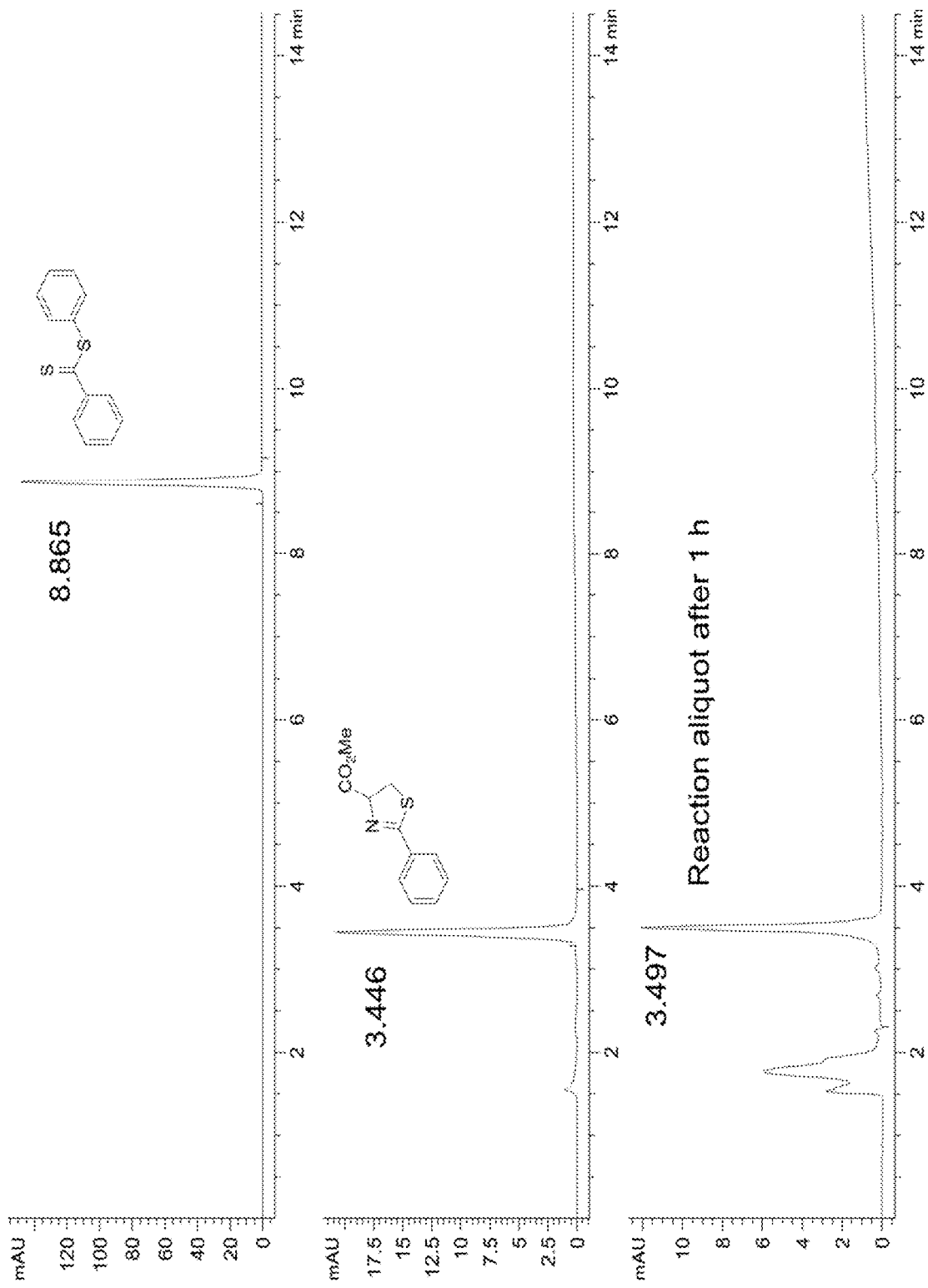
FIG. 12 is a combined HPLC trace providing HPLC traces for reaction products under the following reaction conditions: 100 ppm of compound 506a in hexanes (top trace); 100 μM CysDHT in PBS (10 mM, pH 7.4) with 10% THF (middle trace); and a reaction aliquot after 1 hour (bottom trace).

To a 20 mL solution of 10% THF in PBS (10 mM, pH 7.4) containing 2 mM L-cysteine methyl ester (20 equivalents), 20 mL of 100 mM compound 506a in THF was added for 100 mM compound 506a and stirred at room temperature. After 1 hour, a 1 mL reaction aliquot was analyzed by HPLC. HPLC analysis was performed on an Agilent 1260 HPLC instrument with a Poroshell 120 EC-C18 4.6×100 mm column and monitored at 280 nm. Solvent A: 95% H$_2$O, 5% MeOH, Solvent B: 100% MeCN. Gradient: 35% Solvent A/65% Solvent B for 2 minutes. Change to 100% Solvent B over 4 min and hold for 6.5 minutes. Change to 35% Solvent A/65% Solvent B over 0.5 min and hold for 4.5 minutes. Flow Rate: 0.5 mL/min, 2 μL injection. Results are shown in FIG. 12. The concentration of CysDHT present at the end of the reaction was determined by measurement against calibration curves for each compound (see FIG. 4).

Example 8

Figure 13:
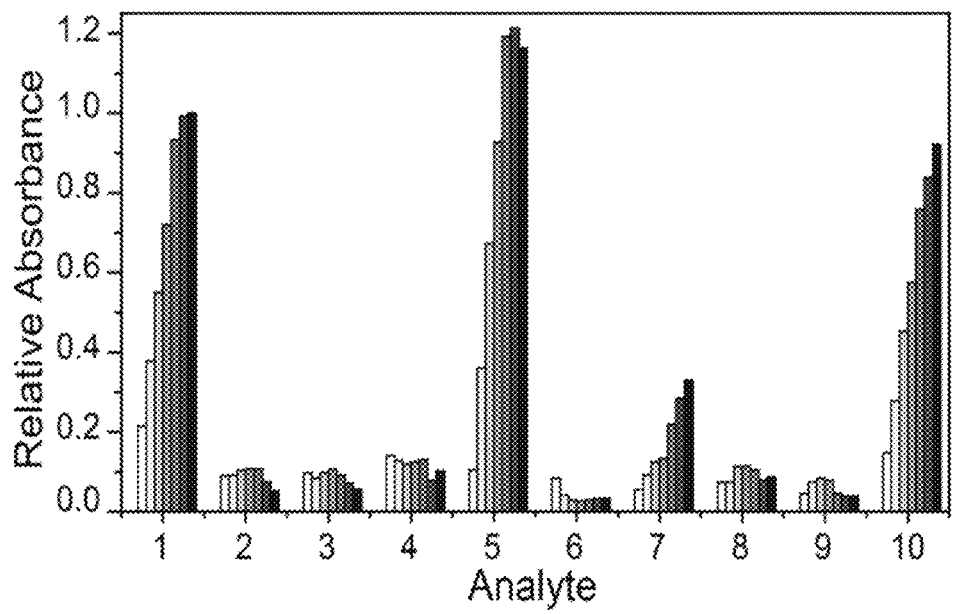
FIG. 13 is a bar graph showing results from determining the selectivity of $H_2S$ release from compound 506a in the presence of different analytes, wherein data were acquired at 1, 5, 10, 15, 30, 45, and 60 minutes and methylene blue absorbance values are relative to the maximum absorbance value obtained from H₂S release in the presence of cysteine.

To further probe the reactivity of dithioester compound embodiments with respect to H$_2$S release, the effect of cysteine derivatives and related thiol-based nucleophiles on H$_2$S release from compound 506a was evaluated (FIG. 13). In the absence of nucleophiles, H$_2$S release was not observed under hydrolytic conditions. Although the conversion of a thiocarbonyl to the corresponding carbonyl is thermodynamically favorable with an enthalpic gain of ~43 kcal/mol when comparing C=S versus C=O bond strengths, the hydrolysis of dithioesters is a slow process and can be considered negligible when considering the rate of cysteine-triggered H$_2$S release. Masking of either the thiol or amine moieties in cysteine reduced H$_2$S release from compound 506a in some embodiments. Additionally, using cysteine methyl ester did not affect H$_2$S release when compared to H$_2$S release in the presence of cysteine. To assess the effect of cysteine analogues on H$_2$S release, H$_2$S release in the presence of homocysteine and penicillamine was measured. Interestingly, a reduction in the H$_2$S release rate in the presence of homocysteine was observed relative to cysteine-triggered H$_2$S release. In the presence of penicillamine, significant H$_2$S release was not observed, likely due to a reduction in the nucleophilicity due to the presence of geminal methyl groups.

The release of H$_2$S from compound 506a in the presence of reduced glutathione (GSH), the most abundant biological thiol, also was evaluated to determine the effect of competitive thiols on H$_2$S release. In the presence of 500 μM GSH, a significant H$_2$S release was not observed, but it also could not rule out that transthioesterification by GSH may take place, which would result in consumption of the dithioester moiety with a lack of H$_2$S release. Considering the nucleophilicity of the departing thiophenol, it currently is believed that the reversibility of transthioesterification is likely to be more efficient for dithioesters, which should result in enhanced selectivity for cysteine over GSH. To evaluate this reactivity H$_2$S release from compound 506a in the presence of 500 μM cysteine and 1 mM GSH was measured. Minimal change on the cysteine-triggered H$_2$S release from compound 506a was observed, even in the presence of excess GSH. These data were used to propose the mechanism detailed in Scheme 7A.

Example 9

Figure 14A:
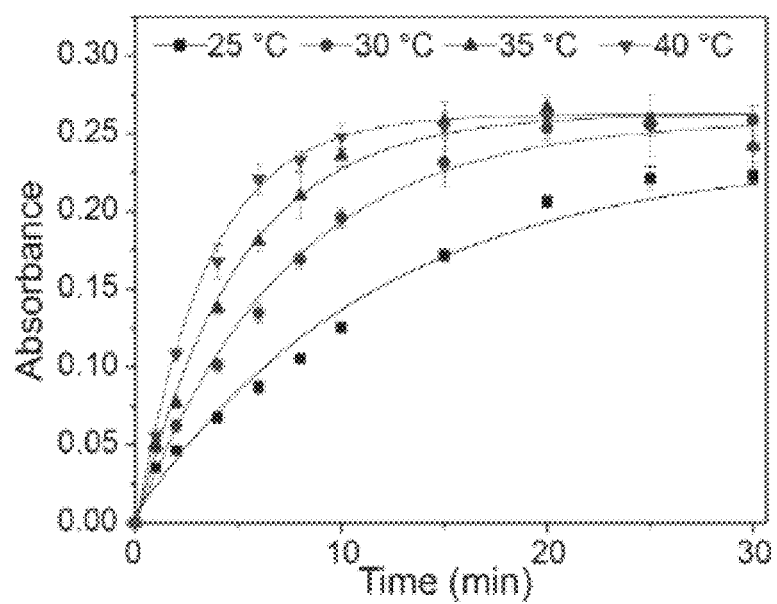
FIGS. 14A and 14B are graphs showing results from evaluating the effect of temperature on rate of H₂S release from compound 506a (25 µM) in the presence of cysteine (500 µM, 20 equivalents) (FIG. 14A) and Eyring analysis of cysteine-triggered H₂S release from compound 506a (FIG. 14B).
Figure 14B:
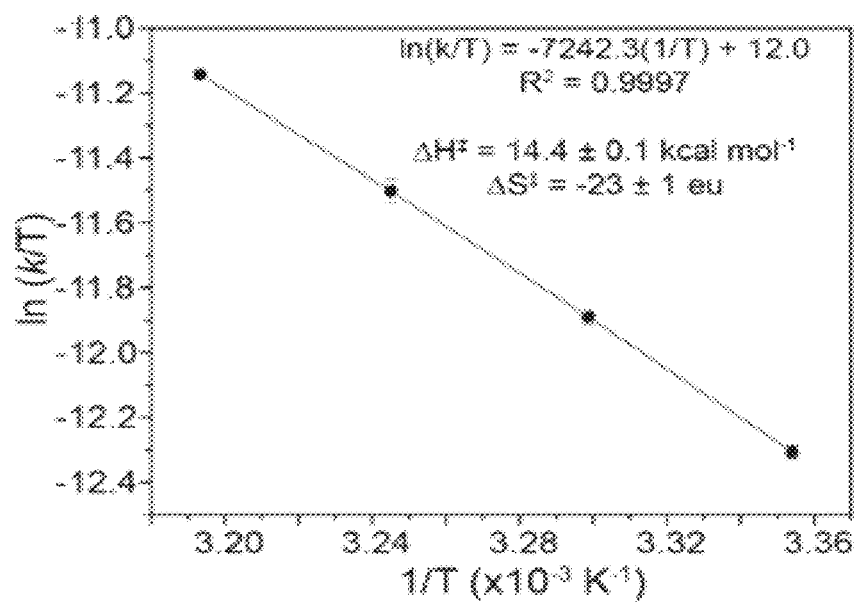

To confirm the formation of a cysteine-based dihydrothiazole, compound 506a (100 μM) was treated with L-cysteine methyl ester (2 mM, 20 equivalents) and a reaction aliquot after 1 hour was subjected to HPLC analysis. In agreement with the mechanism proposed in Scheme 7A, the HPLC analysis revealed the formation of the expected dihydrothiazole in ~61% yield, which is consistent with the H$_2$S-releasing efficiency of compound 506a as measured via the methylene blue assay. To gain insights on the rate-determining step, the effect of temperature on the rate of H$_2$S release from compound 506a (25 μM) in the presence of cysteine (500 μM, 20 equivalents) was measured (FIGS. 14A and 14B). If nucleophilic attack by cysteine on compound 506a is the rate-determining step of the reaction, an entropy of activation (ΔS$^{\ddagger}$) of approximately −20 eu, would be observed, which would be characteristic of a bimolecular reaction.

Upon measuring the rates of H$_2$S release at different temperatures, an Eyring plot was constructed using the obtained k$_{obs}$ values, which afforded ΔS$^{\ddagger}$=−23±1 eu. The observed ΔS$^{\ddagger}$ supports the mechanism proposed in Scheme 7A and is consistent with the initial addition of cysteine to the dithioester to generate 1 being the rate-determining step of cysteine-triggered H$_2$S release from dithioesters. In the reaction of thionoesters with cysteine, an experimentally-determined ΔS$^{\ddagger}$=−38±3 eu was interpreted, suggesting the intramolecular cyclization as the rate determining step. In comparison between both mechanisms, by simply altering the nucleophilicity of the leaving group (i.e. alcohol vs. thiol) the rate-determining step can be shunted.

Figure 15:
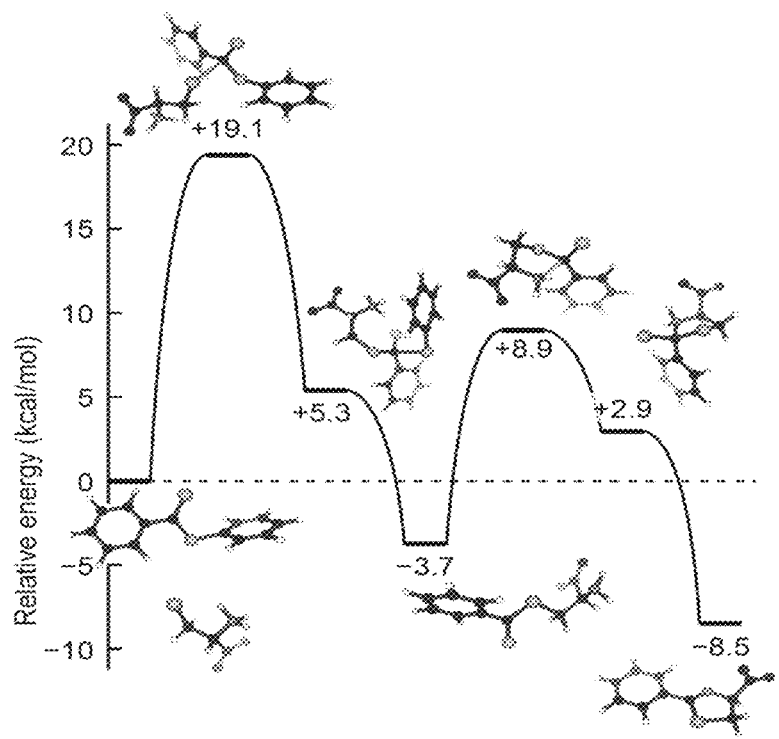

Density functional theory (DFT) was used to examine the potential energy surface for $H_2S$ release from dithioester compound embodiments. Because compound 506a was used for the mechanistic investigations, the reaction of compound 506a with cysteine thiolate was investigated using Gaussian 09 at the B3LYP/6-311++G(d,p) level of theory applying the IEF-PCM water solvation model. The initial nucleophilic attack by cysteine thiolate on compound 506a was found to result in an activation barrier of 19.1 kcal/mol, which was the highest barrier on the reaction coordinate and qualitatively agrees with the experimentally-observed $\Delta H^\ddagger$ of 14.4 kcal/mol. The resultant transthioesterified cysteine adduct is 3.7 kcal/mol more stable than the compound 506a starting material, and subsequently undergoes an intramolecular S to N thioacyl transfer reaction with an associated barrier of 8.9 kcal/mol, resulting in the final and more thermodynamically-favorable dihydrothiazole product. FIG. 15 provides a potential energy surface diagram for the attack of cysteine thiolate on compound 506a.

Example 10

Figure 16:
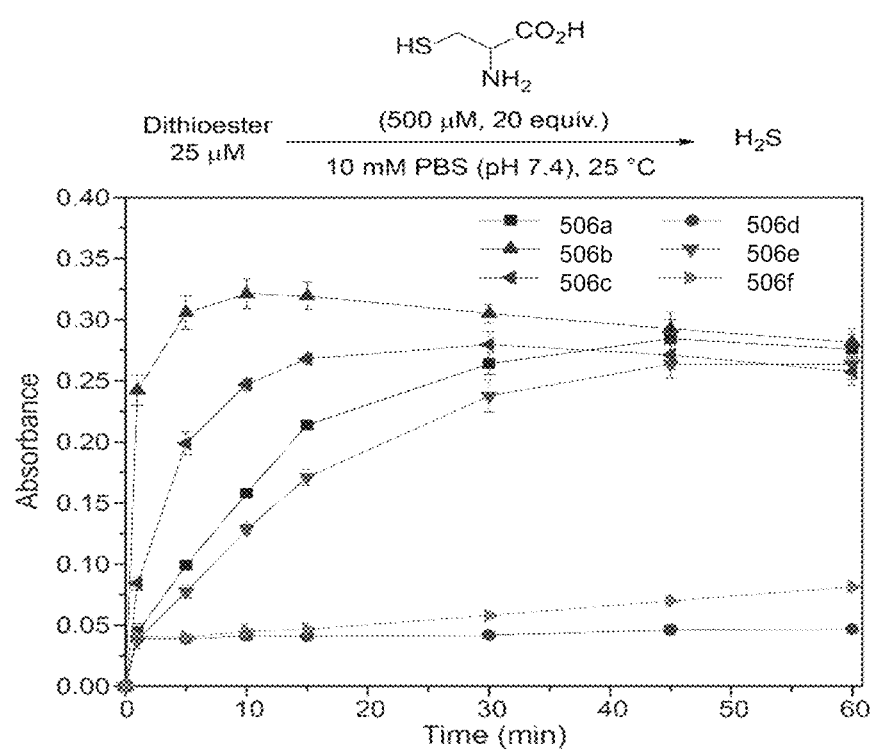
FIG. 16 is a graph showing results from evaluating the effect of alkyl functionalization on the rate of H₂S release from compounds 506a-506f.

In this example, the effect of alkyl functionalization on $H_2S$ release rate and the effect of modifying the thiolate fragment's (produced during activation) nucleophilicity was evaluated. In particular, the effect of inductively donating alkyl groups, such as methyl and isopropyl, was examined, along with replacing the thiophenol with benzyl mercaptan. Results from evaluating $H_2S$ release from a library of alkyl functionalized dithioesters (25 µM) in the presence of cysteine (500 µM, 20 equivalents) are shown in FIG. 16.

Surprisingly, in some embodiments, the presence of inductively-donating alkyl groups led to enhanced rates of $H_2S$ release relative to compound 506a. This result was rationalized by considering the stability of the charge-separated thiocarbonyl motif and the effect of different alkyl groups. In the case of compound 506a, a charge-separated thiocarbonyl yields a benzylic carbocation which can readily delocalize via resonance effectively altering the electrophilicity of the thiocarbonyl via delocalization of the carbocation. In the presence of inductively donating groups such as methyl and isopropyl in compound 506b and compound 506c respectively, the resulting carbocation is localized to the thiocarbonyl position, which would result in enhanced rates of $H_2S$ release in comparison to compound 506a. Incorporation of an isopropyl group in compound 506c, however, also introduces the potential for an intermediate 1,2-methyl shift which would partially delocalize the carbocation and hinder $H_2S$ release relative to compound 506b. Considering these contributions, the enhanced release of $H_2S$ from alkyl-functionalized dithioesters was interpreted as a reflection of altered thiocarbonyl electrophilicity via carbocation delocalization. In addition, the effect of benzyl mercaptan as a leaving group on $H_2S$ release from compound 506e, compound 506d, and compound 506f respectively, was examined. In comparison to thiophenol, benzyl mercaptan is a considerably better nucleophile and likely perturbs the equilibrium of transthioesterification to disfavor the addition of cysteine. $H_2S$ release was observed exclusively from compound 506e. Considering the lack of carbocation delocalization by the pendant methyl group, this result suggests the thiocarbonyl moiety in compound 506e is sufficiently electrophilic to promote $H_2S$ release in the presence of cysteine. Alternatively, minimal $H_2S$ release from compound 506d and relatively slow $H_2S$ release from compound 506f was observed. While this example provided surprising results, it also demonstrates the ability to tune the rate of $H_2S$ release from dithioesters, which can be used to provide dithioesters with predictable rates of $H_2S$ release for use in cellulo or in vivo.

Example 11

In addition to using the donor compound embodiments as an $H_2S$ releasing platform, this example establishes that the donor compound embodiments can be used to couple $H_2S$ release and bioconjugation, such as bioconjugation with biomolecules (e.g., proteins, such as proteins comprising, or modified to comprise, an N-terminus cysteine residue). In this example, using a donor compound embodiment comprising a detectable label, a protein of interest containing an N-terminal cysteine residue is selectively tagged with the detectable label. Notably, enzymatic transformations are known that post-translationally modify terminal cysteine residues to dihydrothiazole moieties, suggesting a high level of biocompatibility for this bioconjugation method. As an example of such applications, this method would be readily compatible with the commonly-used biotin/streptavidin system, in which a biotin-functionalized donor compound embodiment can be reacted with a protein and thus append the biotin biochemical label to the protein and also promote $H_2S$ release. The reactive compound conjugate could be subsequently isolated upon treatment with a streptavidin-based stationary phase. Similarly, such bioconjugation methods can used to enable protein detection. In such a system, a fluorophore-functionalized donor compound embodiment would allow for the selective detection of proteins containing an N-terminus cysteine residue upon fluorescent gel imaging.

Example 12

In this example, a donor compound is administered to a subject by preparing a pharmaceutical composition comprising the donor compound and a pharmaceutically acceptable excipient. The composition is administered either by administering an oral dosage form comprising the composition to the subject, by injecting the composition at a site of interest, by intraperitoneal injection, or by applying a topical ointment comprising the composition at a site of interest. The subject is evaluated for an increase in concentration of $H_2S$ by taking a blood sample from the subject and determining the concentration of $H_2S$ in the blood sample as compared to a blood sample taken from the subject prior to administration of the pharmaceutical composition comprising the donor compound.

Example 13

In this example, a donor compound is administered to a sample by exposing the sample to a composition comprising the donor compound. The sample is then optionally exposed to a separate composition comprising a reactive compound. The sample is evaluated to determine if a detectable signal is emitted within the sample after exposure to the composition comprising the donor compound. In some embodiments, an ELISA assay is used. The evaluation step can comprise analyzing the sample using a spectrofluorometer, a fluorescent microscope, a fluorescence scanner, or a flow cytometer.

In view of the many possible embodiments to which the principles of the disclosed invention may be applied, it should be recognized that the illustrated embodiments are only preferred examples of the invention and should not be

We claim:
1. A compound, wherein the compound is
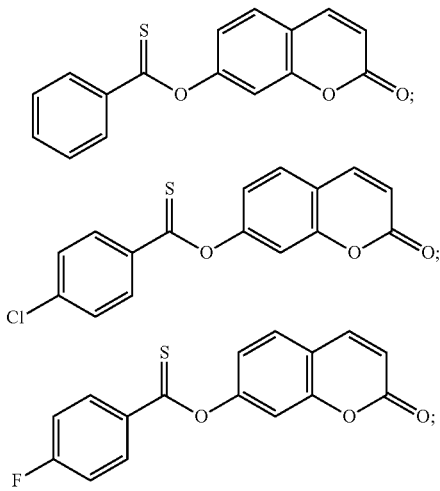
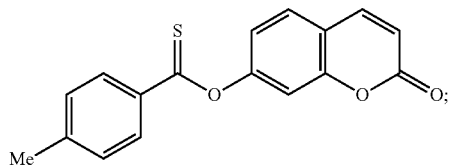
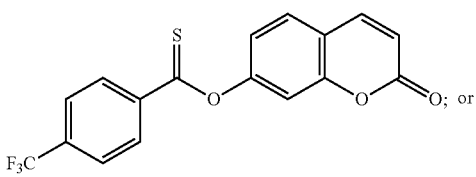
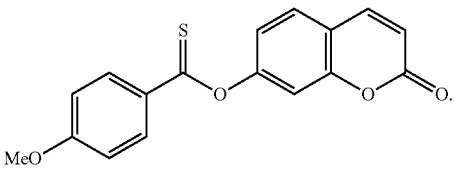
2. A pharmaceutical composition, comprising a compound according to claim 1, and a pharmaceutically acceptable excipient.
* * * * *